US010258507B2

(12) United States Patent
Gonzalez et al.

(10) Patent No.: US 10,258,507 B2
(45) Date of Patent: Apr. 16, 2019

(54) METHODS AND SYSTEMS FOR LASER SCAN LOCATION VERIFICATION AND LASER SURGICAL SYSTEMS WITH LASER SCAN LOCATION VERIFICATION

(71) Applicant: OptiMedica Corporation, Sunnyvale, CA (US)

(72) Inventors: Javier G. Gonzalez, Palo Alto, CA (US); John S. Hart, San Carlos, NM (US)

(73) Assignee: OPTIMEDICA CORPORATION, Santa Ana, CA (US)

( * ) Notice: Subject to any disclaimer, the term of this patent is extended or adjusted under 35 U.S.C. 154(b) by 20 days.

(21) Appl. No.: 14/969,363

(22) Filed: Dec. 15, 2015

(65) Prior Publication Data

US 2017/0011501 A1 Jan. 12, 2017

Related U.S. Application Data

(60) Provisional application No. 62/190,227, filed on Jul. 8, 2015.

(51) Int. Cl.
*G06K 9/00* (2006.01)
*A61F 9/008* (2006.01)
(Continued)

(52) U.S. Cl.
CPC ...... *A61F 9/00814* (2013.01); *A61F 9/00825* (2013.01); *G06T 7/0012* (2013.01); *G06T 7/70* (2017.01); *A61F 2009/0087* (2013.01); *A61F 2009/00844* (2013.01); *A61F 2009/00855* (2013.01); *A61F 2009/00872* (2013.01);
(Continued)

(58) Field of Classification Search
CPC ............ G06T 2207/30004; G06T 2207/30041
See application file for complete search history.

(56) References Cited

U.S. PATENT DOCUMENTS 5,098,426 A 3/1992 Sklar et al.
5,720,894 A 2/1998 Neev et al.
(Continued)

FOREIGN PATENT DOCUMENTS

AU 2015202386 A1 6/2015
WO 2014158615 A1 10/2014

OTHER PUBLICATIONS

Yilmaz et al. ("Object tracking: A survey", 2006)W.*
(Continued)

*Primary Examiner* — Avinash Yentrapati
(74) *Attorney, Agent, or Firm* — Johnson & Johnson Surgical Vision, Inc.

(57) ABSTRACT

A method of verifying a laser scan at a predetermined location within an object includes imaging at least a portion of the object, the resulting image comprising the predetermined location; identifying the predetermined location in the image, thereby establishing an expected scan location of the laser scan in the image; performing a laser scan on the object by scanning a focal point of the laser beam in a scanned area; detecting a luminescence from the scanned area and identifying an actual scanned location within the image based on the detected luminescence; and determining whether the difference between the actual scanned location and the expected scan location is within a threshold value.

36 Claims, 14 Drawing Sheets

(51) Int. Cl.
  *G06T 7/00* (2017.01)
  *G06T 7/70* (2017.01)
(52) U.S. Cl.
  CPC ............... *A61F 2009/00887* (2013.01); *A61F 2009/00889* (2013.01); *A61F 2009/00897* (2013.01); *G06T 2207/30041* (2013.01)

(56) References Cited

U.S. PATENT DOCUMENTS

| | | | |
|---|---|---|---|
| 5,957,915 | A | 9/1999 | Trost |
| 5,984,916 | A | 11/1999 | Lai |
| 6,019,472 | A | 2/2000 | Koester et al. |
| 6,454,761 | B1 | 9/2002 | Freedman |
| 6,802,837 | B2 | 10/2004 | Donitzky et al. |
| 7,655,002 | B2 | 2/2010 | Myers et al. |
| 7,717,907 | B2 | 5/2010 | Ruiz et al. |
| 8,262,646 | B2 | 9/2012 | Frey et al. |
| 8,350,183 | B2 | 1/2013 | Vogel et al. |
| 8,382,745 | B2 | 2/2013 | Naranjo-Tackman et al. |
| 8,414,564 | B2 | 4/2013 | Goldshleger et al. |
| 9,549,670 | B2* | 1/2017 | Gonzalez ............... A61B 3/107 |
| 2004/0054359 | A1 | 3/2004 | Ruiz et al. |
| 2006/0195076 | A1* | 8/2006 | Blumenkranz ..... A61F 9/00736 606/4 |
| 2011/0172649 | A1 | 7/2011 | Schuele |
| 2011/0319873 | A1 | 12/2011 | Raksi et al. |
| 2011/0319875 | A1 | 12/2011 | Loesel et al. |
| 2012/0150157 | A1* | 6/2012 | Wolfel ............... A61F 9/00825 606/4 |
| 2012/0314224 | A1 | 12/2012 | Luellau |
| 2013/0015370 | A1* | 1/2013 | Damaskinos ...... G01N 21/6452 250/459.1 |
| 2013/0211387 | A1 | 8/2013 | Riedel et al. |
| 2014/0128731 | A1* | 5/2014 | Gonzalez ............... A61B 3/107 600/427 |
| 2014/0128821 | A1 | 5/2014 | Gooding |
| 2014/0128853 | A1 | 5/2014 | Angeley |
| 2014/0163534 | A1 | 6/2014 | Angeley |
| 2014/0257255 | A1 | 9/2014 | Lee |
| 2014/0316389 | A1* | 10/2014 | Schuele ............... A61F 9/00804 606/5 |
| 2015/0141972 | A1* | 5/2015 | Woodley ............... A61B 3/102 606/5 |
| 2015/0150721 | A1* | 6/2015 | Schuele ............... A61F 9/00804 606/3 |
| 2015/0216730 | A1* | 8/2015 | Schuele ............... A61F 9/00834 606/6 |
| 2015/0272782 | A1 | 10/2015 | Schuele |
| 2015/0282988 | A1 | 10/2015 | Simoneau |
| 2017/0087019 | A1* | 3/2017 | Gonzalez ............... A61B 3/107 |

OTHER PUBLICATIONS

Pleijhuis et al. ("Tissue-simulating Phantoms for Assessing Potential Near-infrared Fluorescence Imaging Applications in Breast Cancer Surgery"), 2014.*
Baeten et al. ("Development of fluorescent materials for Diffuse Fluorescence Tomography standards and phantoms"), 2007.*
Yilmaz et al. ("Object Tracking: A Survey"), 2006.*
International Search Report and Written Opinion for Application No. PCT/US2015/065724, dated Mar. 15, 2016, 14 pages.
De Loor R., "Polygon Scanner System for Ultra Short Pulsed Laser Micro-Machining Applications," Physics Procedia, 2013, vol. 41, pp. 544-551.
Zhang D., et al., "Applications of Digital Image Correlation to Biological Tissues," Journal of Biomedical Optics, 2004, vol. 9 (4), pp. 691-699.

* cited by examiner

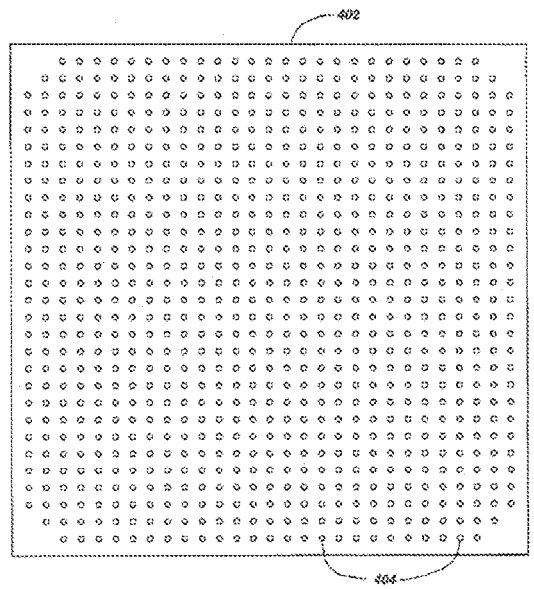
FIG. 7A
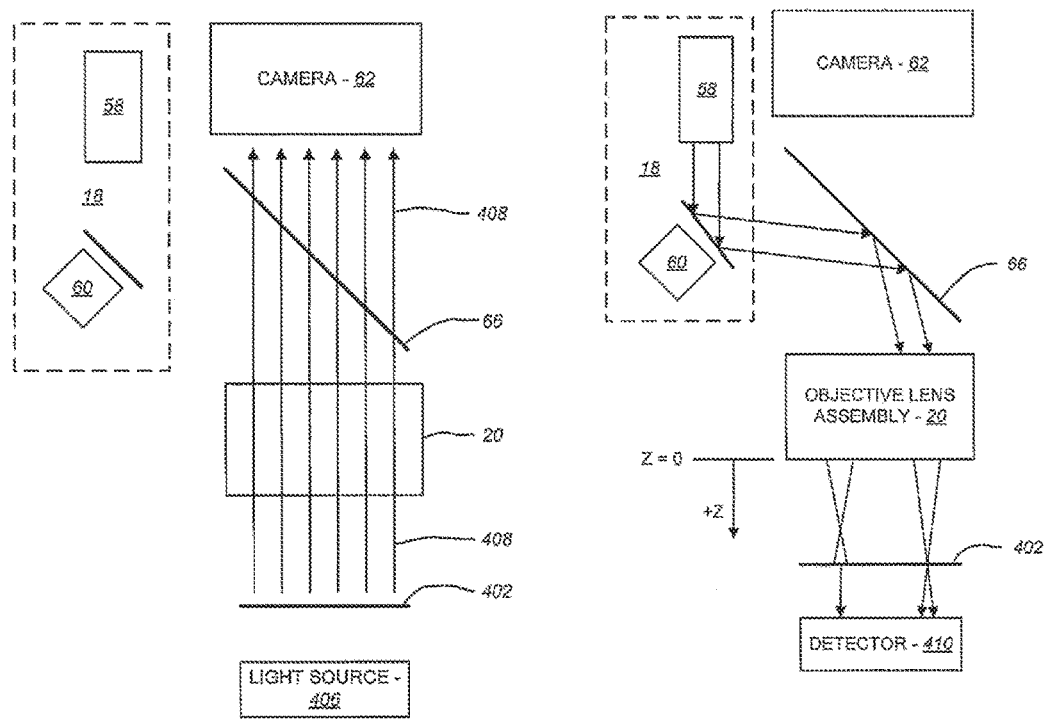
FIG. 7B
FIG. 7C

METHODS AND SYSTEMS FOR LASER SCAN LOCATION VERIFICATION AND LASER SURGICAL SYSTEMS WITH LASER SCAN LOCATION VERIFICATION

RELATED APPLICATIONS

This application is a non-provisional application and claims the benefit under 35 U.S.C. § 119(e) of U.S. Provisional Application Ser. No. 62/190,227, filed Jul. 8, 2015, which is incorporated herein in its entirety by reference.

BACKGROUND

Cataract extraction is a frequently performed surgical procedure. A cataract is formed by opacification of the crystalline lens of the eye. The cataract scatters light passing through the lens and may perceptibly degrade vision. A cataract can vary in degree from slight to complete opacity. Early in the development of an age-related cataract the power of the lens may increase, causing near-sightedness (myopia). Gradual yellowing and opacification of the lens may reduce the perception of blue colors as those shorter wavelengths are more strongly absorbed and scattered within the cataractous crystalline lens. Cataract formation may often progress slowly resulting in progressive vision loss.

A cataract treatment may involve replacing the opaque crystalline lens with an artificial intraocular lens (IOL), and an estimated 19 million cataract surgeries per year are performed worldwide. Cataract surgery can be performed using a technique termed phacoemulsification in which an ultrasonic tip with associated irrigation and aspiration ports is used to sculpt the relatively hard nucleus of the lens to facilitate removal through an opening made in the anterior lens capsule. The nucleus of the lens is contained within an outer membrane of the lens that is referred to as the lens capsule. Access to the lens nucleus can be provided by performing an anterior capsulotomy in which a small round hole can be formed in the anterior side of the lens capsule. A primary incision and a sideport incision may be placed in the cornea to allow access for the ultrasonic tip or other instruments and to permit removal of the lens pieces. An arcuate incision may also be placed in the cornea during cataract surgery to alter the refractive properties of the cornea. After removal of the lens nucleus, a synthetic foldable intraocular lens (TOL) can be inserted into the remaining lens capsule of the eye.

Accurate placement of a capsulotomy incision, a primary incision, a sideport incision and an arcuate incision can be important for achieving a successful outcome of cataract surgery. In automated laser surgical procedures, physicians generally provide the necessary parameters for identifying the number, placement and size of incisions based on pre-treatment measurements. However, errors in data entry or lack of proper calibration of the laser surgical system can potentially lead to the placement of incisions at locations other than at the locations prescribed by the user. Moreover, some laser surgery systems have not allowed real time confirmation of the location of the incision at the predetermined location or have not provided warnings to the user if the actual placement of incisions during an automated scan is different from the intended location of the incisions.

Thus, methods and systems that introduce additional safeguards, such as verifying the location of a laser scan or ocular incision, would be helpful for treating patients with laser surgical systems.

SUMMARY OF THE INVENTION

Hence, to obviate one or more problems due to limitations and disadvantages of the related art, this disclosure provides embodiments, including a method of verifying the placement of a laser scan at a predetermined location within an object comprises imaging at least a portion of the object, the resulting image comprising the predetermined location; identifying the predetermined location in the image, thereby establishing an expected scan location of the laser scan in the image; performing the laser scan on the object by scanning a focal point of a laser beam in a scanned area; detecting a luminescence from the scanned area and identifying an actual scanned location within the image based on the detected luminescence; and verifying whether the laser scan was at the predetermined location based on a difference between the actual scanned location and expected scan location. Preferably, the laser beam is a pulsed laser beam having a wavelength of 320 nm to 370 nm. The luminescence preferably has a wavelength of 400 nm or more. The step of verifying the laser scan is at the predetermined location comprises determining whether a distance between the actual scanned location and the expected scan location is within a predetermined threshold.

In many embodiments, the object is a human eye. In other embodiments, the object is a calibration apparatus.

In many embodiments, the image comprises an array of pixels. The expected scan location preferably comprises one or more pixels selected from amongst the array of pixels. Also, the actual scanned location preferably comprises one or more pixels selected from the array of pixels. Preferably, verifying the laser scan at the predetermined location comprises determining whether a distance between the actual scanned location and the expected scan location is within a predetermined threshold.

In many embodiments, the method further comprises periodically re-imaging the object, thereby obtaining one or more successive images of the object, and identifying an actual scanned location by comparing a detected luminescence of a same pixel in the array between two of the successive images. Preferably, the methods include identifying a direction of the scan by comparing an actual scanned location in between two or more of the successive images. A method of verifying the placement of an ocular incision by a laser surgical system at a predetermined location within an eye comprises imaging at least a portion of the eye, the resulting image comprising the predetermined location for a laser scan corresponding to the ocular incision; identifying the predetermined location in the image, thereby establishing an expected scan location of the ocular incision in the image; performing a laser scan on the object by scanning a focal point of the laser beam in a scanned area, the laser scan being configured in a scan pattern for performing the ocular incision; detecting a luminescence from the scanned area and identifying an actual scanned location within the image based on the detected luminescence; and verifying the placement of an ocular incision based on the difference between the actual scanned location and expected scan location. The luminescence preferably has a wavelength of 400 nm or more. The step of verifying the laser scan is at the predetermined location comprises determining whether a distance between the actual scanned location and the expected scan location is within a predetermined threshold.

In many embodiments, the image comprises an array of pixels. The expected scan location preferably comprises one or more pixels selected from amongst the array of pixels. Also, the actual scanned location preferably comprises one or more pixels selected from the array of pixels. Preferably, verifying the laser scan at the predetermined location comprises determining whether a distance between the actual scanned location and the expected scan location is within a predetermined threshold.

In many embodiments, the method further comprises periodically re-imaging the object, thereby obtaining one or more successive images of the eye, and identifying an actual scanned location by comparing a detected luminescence of a same pixel in the array between two of the successive images. Preferably, the methods include identifying a direction of the scan by comparing an actual scanned location in between two or more of the successive images.

In many embodiments, a method of verifying the calibration of a laser eye surgical system comprises imaging at least a portion of a calibration apparatus having at least one emissive surface, the resulting image comprising a predetermined location for a laser scan; identifying the predetermined location in the image, thereby establishing an expected scan location of the laser scan in the image; performing the laser scan of the calibration apparatus by scanning a focal point of the laser beam in a scanned area; detecting a luminescence from the scanned area and identifying an actual scanned location within the image based on the detected luminescence; and determining whether the laser surgical system is calibrated based on a difference between the actual scanned location and expected scan location. The laser beam preferably has a wavelength of 320 nm to 370 nm. The luminescence preferably has a wavelength of 400 nm or more. The step of verifying the laser scan is at the predetermined location preferably comprises determining whether a distance between the actual scanned location and the expected scan location is within a predetermined threshold.

In many embodiments, the image comprises an array of pixels. The expected scan location preferably comprises one or more pixels selected from amongst the array of pixels. Also, the actual scanned location preferably comprises one or more pixels selected from the array of pixels. Preferably, verifying the laser scan at the predetermined location comprises determining whether a distance between the actual scanned location and the expected scan location is within a predetermined threshold.

In many embodiments, the method further comprises periodically re-imaging the object, thereby obtaining one or more successive images of the calibration apparatus, and identifying an actual scanned location by comparing a detected luminescence of a same pixel in the array between two of the successive images. Preferably, the methods include identifying a direction of the scan by comparing an actual scanned location in between two or more of the successive images.

In many embodiments, a laser eye surgical system, comprises a laser source for generating a pulsed laser beam; an imaging system comprising a detector; shared optics configured for directing the pulsed laser beam to an object to be sampled and confocally deflecting back-reflected light from the object to the detector; and a controller operatively coupled to the laser source, the imaging system and the shared optics. The controller configured to: receive one or more parameters defining one or more ocular incisions; image the eye with the imaging apparatus and identify an expected scan location within the image corresponding to the one or more ocular incisions based on the one or more parameters; scan the focal point of a laser beam; detect luminescence from the region scanned; identify the actual scanned location within the image based on the detected luminescence; and provide a warning to the user if a difference between the actual scanned location and the expected is not within a predetermined threshold value.

The controller may be configured to verify the laser scan is at the predetermined location when a distance between the actual scanned location and the expected scan location is within a predetermined threshold.

The laser beam preferably has a wavelength of 320 nm to 370 nm, and the luminescence has a wavelength of 400 nm or more.

In may embodiments, the image preferably comprises an array of pixels. The expected scan location preferably comprises one or more pixels selected from amongst the array of pixels, and the actual scanned location comprises one or more pixels selected from the array of pixels.

The controller is preferably configured to periodically re-image the eye, thereby obtaining one or more successive images and identifying an actual scanned location by comparing a detected luminescence of a same pixel in the array between two of the successive images. The controller is also preferably configured to identify direction of the scan by comparing an actual scanned location in between two or more of the successive images.

This summary and the following detailed description are merely exemplary, illustrative, and explanatory, and are not intended to limit, but to provide further explanation of the invention as claimed. Additional features and advantages of the invention will be set forth in the descriptions that follow, and in part will be apparent from the description, or may be learned by practice of the invention. The objectives and other advantages of the invention will be realized and attained by the structure particularly pointed out in the written description, claims and the appended drawings.

BRIEF DESCRIPTION OF THE FIGURES

The novel features of the invention are set forth with particularity in the appended claims. A better understanding of the features and advantages will be facilitated by referring to the following detailed description that sets forth illustrative embodiments using principles of the invention, as well as to the accompanying drawings, in which like numerals refer to like parts throughout the different views. Like parts, however, do not always have like reference numerals. Further, the drawings are not drawn to scale, and emphasis has instead been placed on illustrating the principles of the invention. All illustrations are intended to convey concepts, where relative sizes, shapes, and other detailed attributes may be illustrated schematically rather than depicted literally or precisely.

FIG. 7A is a plan view illustrating a calibration plate according to many embodiments that can be used to calibrate the laser surgery system of FIG. 1.

FIG. 7B is a schematic diagram illustrating using the calibration plate of FIG. 10A to calibrate a camera of the laser surgery system of FIG. 1.

FIG. 7C is a schematic diagram illustrating using the calibration plate of FIG. 10A to calibrate the scanning assembly of the laser surgery system of FIG. 1.

DETAILED DESCRIPTION

In the following description, various embodiments of the present invention will be described. For purposes of explanation, specific configurations and details are set forth in order to provide a thorough understanding of the embodiments. It will also, however, be apparent to one skilled in the art that the present invention can be practiced without the specific details. Furthermore, well-known features may be omitted or simplified in order not to obscure the embodiment being described.

Systems for imaging and/or treating an eye of a patient are provided. In many embodiments, a shared optics provides a variable optical path by which a portion of an electromagnetic beam reflected from a focal point disposed within the eye is directed to a path length insensitive imaging assembly, such as a confocal detection assembly. In many embodiments, the shared optics is configured to accommodate movement of the patient while maintaining alignment between an electromagnetic radiation beam and the patient. The electromagnetic radiation beam can be configured for imaging the eye, can be configured for treating the eye, and can be configured for imaging and treating the eye.

Figure 1:
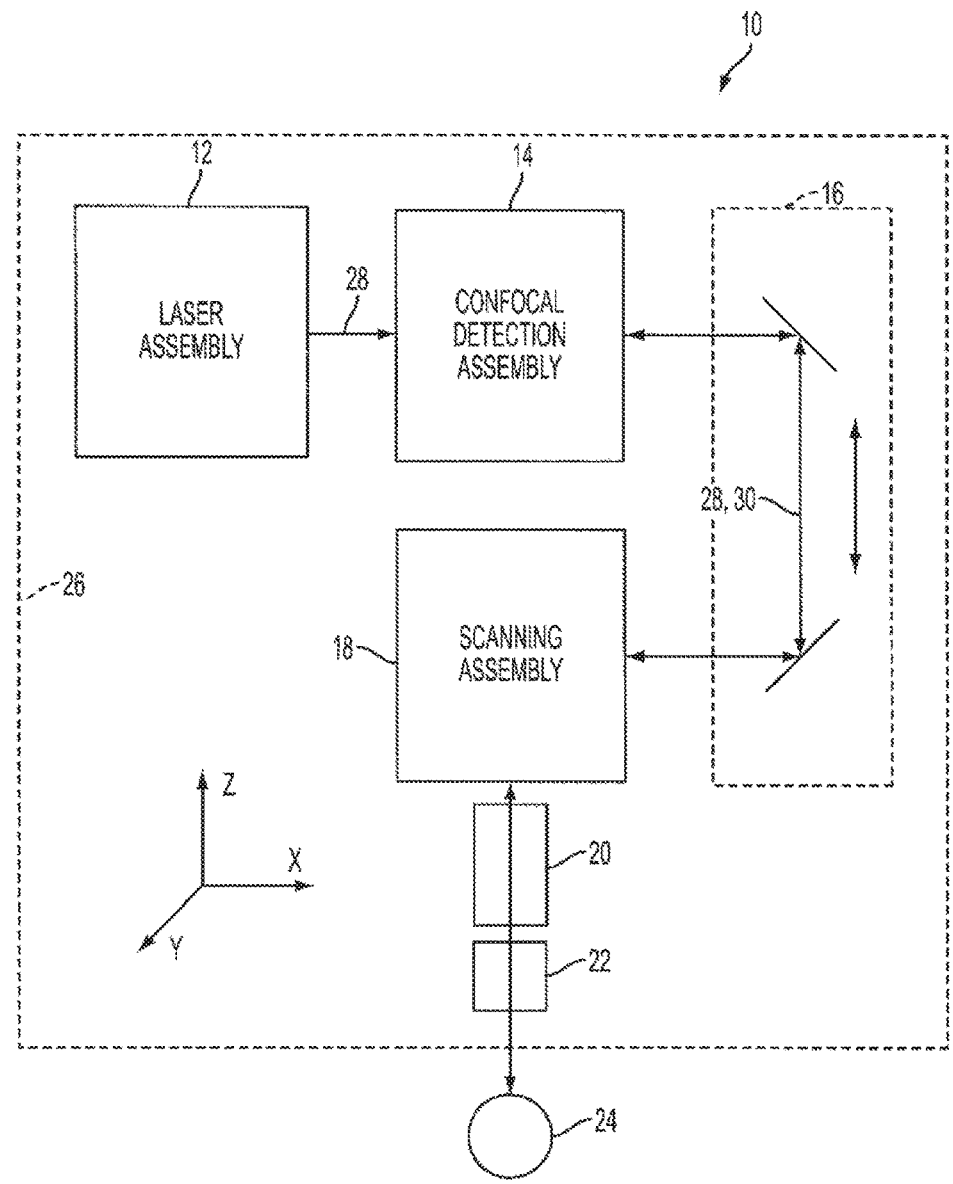
FIG. 1 is a schematic diagram of a laser surgery system according to many embodiments in which a patient interface device is coupled to a laser assembly and a detection assembly by way of a scanning assembly and shared optics that supports the scanning assembly.

Referring now to the drawings in which like numbers reference similar elements FIG. 1 schematically illustrates a laser surgery system 10, according to many embodiments. The laser surgery system 10 includes a laser assembly 12, a confocal detection assembly 14, a shared optics 16, a scanning assembly 18, an objective lens assembly 20, and a patient interface device 22. The patient interface device 22 is configured to interface with a patient 24. The patient interface device 22 is supported by the objective lens assembly 20. The objective lens assembly 20 is supported by the scanning assembly 18. The scanning assembly 18 is supported by the shared optics 16. The shared optics 16 has a portion having a fixed position and orientation relative to the laser assembly 12 and the confocal detection assembly 14. In many embodiments, the patient interface device 22 is configured to interface with an eye of the patient 24. For example, the patient interface device 22 can be configured to be vacuum coupled to an eye of the patient 24 such as described in co-pending U.S. Provisional patent application Ser. No. 14/068,994, entitled "Liquid Optical Interface for Laser Eye Surgery System," filed Oct. 31, 2013. The laser surgery system 10 can further optionally include a base assembly 26 that can be fixed in place or repositionable. For example, the base assembly 26 can be supported by a support linkage that is configured to allow selective repositioning of the base assembly 26 relative to a patient and secure the base assembly 26 in a selected fixed position relative to the patient. Such a support linkage can be supported in any suitable manner such as, for example, by a fixed support base or by a movable cart that can be repositioned to a suitable location adjacent to a patient. In many embodiments, the support linkage includes setup joints with each setup joint being configured to permit selective articulation of the setup joint and can be selectively locked to prevent inadvertent articulation of the setup joint, thereby securing the base assembly 26 in a selected fixed position relative to the patient when the setup joints are locked. In many embodiments, the laser assembly 12 is configured to emit an electromagnetic radiation beam 28. The beam 28 can include a series of laser pulses of any suitable energy level, duration, and repetition rate.

In one embodiment, the laser assembly 12 incorporates femtosecond (FS) laser technology. By using femtosecond laser technology, a short duration (e.g., approximately 10-13 seconds in duration) laser pulse (with energy level in the micro joule range) can be delivered to a tightly focused point to disrupt tissue, thereby substantially lowering the energy level required to image and/or modify an intraocular target as compared to laser pulses having longer durations. In other embodiments, the pulse duration of the laser pulses is generally between 1 ps and 100 ns. The laser assembly 12 can produce laser pulses having a wavelength suitable to treat and/or image tissue. For example, the laser assembly 12 can be configured to emit an electromagnetic radiation beam 28 such as that emitted by any of the laser surgery systems described in co-pending U.S. application Ser. No. 14/069,042, entitled "Laser Eye Surgery System," filed Oct. 31, 2013; U.S. patent application Ser. No. 12/987,069, entitled "Method and System For Modifying Eye Tissue and Intraocular Lenses," filed Jan. 7, 2011; U.S. application Ser. No. 14/576,593, entitled "Confocal Laser Eye Surgery System," filed Dec. 19, 2014; and U.S. application Ser. No. 14/666,743, entitled "Automated Calibration of Laser System and Tomography System with Fluorescent Imaging of Scan Pattern," filed Mar. 24, 2015. For example, the laser assembly 12 can produce laser pulses having a wavelength from 1020 nm to 1050 nm. For example, the laser assembly 12 can have a diode-pumped solid-state configuration with a 1030 (+/5) nm center wavelength. As another example, the laser assembly 12 can produce ultraviolet light pulses having a wavelength of between 320 nm and 430 nm, preferably between 320 and 400 nm, preferably between 320 to 370 nm, and more preferably between 340 nm and 360 nm. In many embodiments, the laser pulses have a wavelength of 355 nm. The 320 nm to 430 nm light source may be, for instance, a Nd:YAG laser source operating at the 3rd harmonic wavelength, 355 nm.

When an ultraviolet wavelength is used, the pulse energy of the laser pulses is generally between 0.01 µJ and 500 µJ. In many embodiments, the pulse energy will be between 0.1 µJ and 100 µJ, or more precisely, between 0.1 µJ and 40 µJ, or between 0.1 µJ and 10 µJ. When an ultraviolet wavelength is used, a pulse repetition rate of the laser pulses is generally between 500 Hz and 500 kHz. In many embodiments, the pulse repetition rate is between 1 kHz to 200 kHz, or between 1 KHz to 100 KHz.

When an ultraviolet wavelength is used, spot sizes of the laser pulses are generally smaller than 10 µm. In many embodiments, the spot size is preferably smaller than 5 µm, typically 0.5 µm to 3 µm.

When an ultraviolet wavelength is used, the pulse duration of the laser pulses is generally between 1 ps and 100 ns. In many embodiments, the pulse duration is between 100 ps to 10 ns, or between 100 ps and 1 ns. In a preferred embodiment, the pulse duration is between 300 ps and 700 ps, preferably 400 ps to 700 ps.

In some embodiments when an ultraviolet wavelength is used, the beam quality, also referred to as M2 factor, is between 1 and 1.3. The M2 factor is a common measure of the beam quality of a laser beam. In brief, the M2 factor is defined as the ratio of a beam's actual divergence to the divergence of an ideal, diffraction limited, Gaussian TEM00 beam having the same waist size and location as is described in ISO Standard 11146.

In some embodiments when an ultraviolet wavelength is used, a peak power density, obtained by dividing the peak power of the laser pulse by the focal spot size, is generally expressed in units of GW/cm2. In general, the peak power density of the laser pulses should be sufficiently high to modify the ocular tissue to be treated. As would be understood by those ordinarily skilled, the peak power density depends upon a number of factors, including the wavelength of the selected laser pulses. In some embodiments, a peak power density is generally in the range of 100 GW/cm2 to 800 GW/cm2 will be used to cut ocular tissue with 355 nm light. In some embodiments when an ultraviolet wavelength is used, the scan range of the laser surgical system is preferably in the range of 6 mm to 10 mm. In some embodiments when an ultraviolet wavelength is used, spot spacing between adjacent laser pulses is typically in the range of about 0.20 µm to 10 µm, preferably 0.2 µm to 6 µm.

In some embodiments when an ultraviolet wavelength is used, a numerical aperture should be selected that preferably provides for the focal spot of the laser beam to be scanned over a scan range of 6 mm to 10 mm in a direction lateral to a Z-axis that is aligned with the laser beam. The NA of the system should be less than 0.6, preferably less than 0.5 and more preferably in a range of 0.05 to 0.4, typically between 0.1 and 0.3. In some specific embodiments, the NA is 0.15. For each selected NA, there are suitable ranges of pulse energy and beam quality (measured as an M2 value) necessary to achieve a peak power density in the range required to cut the ocular tissue. Further considerations when choosing the NA include available laser power and pulse rate, and the time needed to make a cut. Further, in selection of an appropriate NA, it is preferable to ensure that there is a safe incidental exposure of the iris, and other ocular tissues that are not targeted for cuts.

When UV wavelengths are used, the tissue modification is carried out using chromophore absorption without plasma formation and/or without bubble formation and an associated cavitation event. Here, chromophore absorption refers to the absorption of at least a portion of the ultraviolet light by one or more chemical species in the target area. The use of ultraviolet light significantly reduces the threshold for plasma formation and associated formation of cavitation bubbles but also decreases the threshold energy required for linear absorption enhanced photodecomposition without the formation of cavitation bubbles for a few reasons. First, the focused spot diameter scales linearly with wavelength which squares the peak radiant exposure within the focal plane. Second, the linear absorption of the material itself allows an even lower threshold for plasma formation or low density photodecomposition as initially more laser energy is absorbed in the target structure. Third, the use of UV laser pulses in the nanosecond and sub-nanosecond regime enables linear absorption enhanced photodecomposition and chromophore guided ionization.

Furthermore, this chromophore-guided ionization when using ultraviolet wavelength strongly lowers the threshold for ionization in case of plasma formation as well lowers the threshold for low density photodecomposition for material modification or alteration without cavitation even under very weak absorption. The linear absorption also allows for the specific treatment of topical lens structures (e.g. the lens capsule) as the optical penetration depth of the laser beam is limited by the linear absorption of the lens. This is especially true for aged lenses which absorption in the UV-blue spectral region increases strongly compared to young lenses.

The laser assembly 12 can include control and conditioning components. For example, such control components can include components such as a beam attenuator to control the energy of the laser pulse and the average power of the pulse train, a fixed aperture to control the cross-sectional spatial extent of the beam containing the laser pulses, one or more power monitors to monitor the flux and repetition rate of the beam train and therefore the energy of the laser pulses, and a shutter to allow/block transmission of the laser pulses. Such conditioning components can include an adjustable zoom assembly and a fixed optical relay to transfer the laser pulses over a distance while accommodating laser pulse beam positional and/or directional variability, thereby providing increased tolerance for component variation.

In many embodiments, the laser assembly 12 and the confocal detection assembly 14 have fixed positions relative to the base assembly 26. The beam 28 emitted by the laser assembly 12 propagates along a fixed optical path through the confocal detection assembly 14 to the shared optics 16. The beam 28 propagates through the shared optics 16 along a variable optical path 30, which delivers the beam 28 to the scanning assembly 18. In many embodiments, the beam 28 emitted by the laser assembly 12 is collimated so that the beam 28 is not impacted by patient movement induced changes in the length of the optical path between the laser assembly 12 and the scanner 16. The scanning assembly 18 is operable to scan the beam 28 (e.g., via controlled variable deflection of the beam 28) in at least one dimension. In many embodiments, the scanning assembly 18 is operable to scan the beam 28 in two dimensions transverse to the direction of the propagation of the beam 28 and is further operable to scan the location of a focal point of the beam 28 in the direction of propagation of the beam 28. The scanned beam is emitted from the scanning assembly 18 to propagate through the objective lens assembly 20, through the interface device 22, and to the patient 24.

The shared optics 16 is configured to accommodate a range of movement of the patient 24 relative to the laser assembly 12 and the confocal detection assembly 14 in one or more directions while maintaining alignment of the beam 28 emitted by the scanning assembly 18 with the patient 24. For example, in many embodiments, the shared optics 16 is configured to accommodate a range movement of the patient 24 in any direction defined by any combination of unit orthogonal directions (X, Y, and Z).

The shared optics 16 supports the scanning assembly 18 and provides the variable optical path 30, which changes in response to movement of the patient 24. Because the patient interface device 22 is interfaced with the patient 24, movement of the patient 24 results in corresponding movement of the patient interface device 22, the objective lens assembly 20, and the scanning assembly 18. The shared optics 16 can include, for example, any suitable combination of a linkage that accommodates relative movement between the scanning assembly 18 and, for example, the confocal detection assembly 24, and optical components suitably tied to the linkage so as to form the variable optical path 30.

A portion of the electromagnetic radiation beam 28 that is reflected by eye tissue at the focal point propagates back to the confocal detection assembly 14. Specifically, a reflected portion of the electromagnetic radiation beam 28 travels back through the patient interface device 22, back through the objective lens assembly 20, back through (and descanned by) the scanning assembly 18, back through the shared optics 16 (along the variable optical path 30), and to the confocal detection assembly 14. In many embodiments, the reflected portion of the electromagnetic radiation beam that travels back to the confocal detection assembly 14 is directed to be incident upon a sensor that generates an intensity signal indicative of intensity of the incident portion of the electromagnetic radiation beam. The intensity signal, coupled with associated scanning of the focal point within the eye, can be processed in conjunction with the parameters of the scanning to, for example, image/locate structures of the eye, such as the anterior surface of the cornea, the posterior surface of the cornea, the iris, the anterior surface of the lens capsule, and the posterior surface of the lens capsule. In many embodiments, the amount of the reflected electromagnetic radiation beam that travels to the confocal detection assembly 14 is substantially independent of expected variations in the length of the variable optical path 30 due to patient movement, thereby enabling the ability to ignore patient movements when processing the intensity signal to image/locate structures of the eye.

Figure 2:
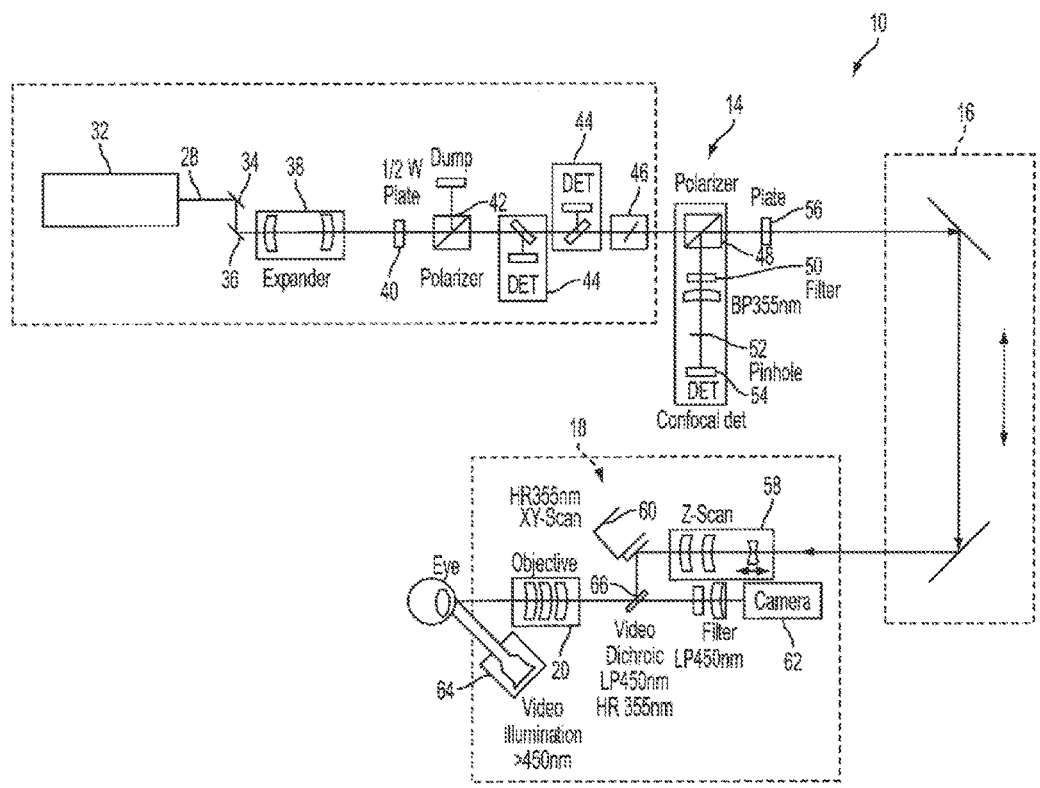
FIG. 2 is a schematic diagram of an embodiment of the laser surgery system of FIG. 1.

FIG. 2 schematically illustrates details of an embodiment of the laser surgery system 10. Specifically, example configurations are schematically illustrated for the laser assembly 12, the confocal detection assembly 14, and the scanning assembly 18. As shown in the illustrated embodiment, the laser assembly 12 can include an laser 32 (e.g., a femtosecond laser), alignment mirrors 34, 36, a beam expander 38, a one-half wave plate 40, a polarizer and beam dump device 42, output pickoffs and monitors 44, and a system-controlled shutter 46. The electromagnetic radiation beam 28 output by the laser 32 is deflected by the alignment mirrors 34, 36. In many embodiments, the alignment mirrors 34, 36 are adjustable in position and/or orientation so as to provide the ability to align the beam 28 with the downstream optical path through the downstream optical components. Next, the beam 28 passes through the beam expander 38, which increases the diameter of the beam 28. Next, the expanded beam 28 passes through the one-half wave plate 40 before passing through the polarizer. The beam exiting the laser is linearly polarized. The one-half wave plate 40 can rotate this polarization. The amount of light passing through the polarizer depends on the angle of the rotation of the linear polarization. Therefore, the one-half wave plate 40 with the polarizer acts as an attenuator of the beam 28. The light rejected from this attenuation is directed into the beam dump. Next, the attenuated beam 28 passes through the output pickoffs and monitors 44 and then through the system-controlled shutter 46. By locating the system-controlled shutter 46 downstream of the output pickoffs and monitors 44, the power of the beam 28 can be checked before opening the system-controlled shutter 46.

As shown in the illustrated embodiment, the confocal detection assembly 14 can include a polarization-sensitive device such as a polarized or unpolarized beam splitter 48, a filter 50, a focusing lens 51, a pinhole aperture 52, and a detection sensor 54. A one-quarter wave plate 56 is disposed downstream of the polarized beam splitter 48. The beam 28 as received from the laser assembly 12 is polarized so as to pass through the polarized beam splitter 48. Next, the beam 28 passes through the one-quarter wave plate 56, thereby rotating the polarization axis of the beam 28. A quarter rotation is a presently preferred rotation amount. After reflecting from the focal point in the eye, the returning reflected portion of the beam 28 passes back through the one-quarter wave plate 56, thereby further rotating the polarization axis of the returning reflected portion of the beam 28. Ideally, after passing back through the one-quarter wave plate 56, the returning reflected portion of the beam has experienced a total polarization rotation of 90 degrees so that the reflected light from the eye is fully reflected by the polarized beam splitter 48. The birefringence of the cornea can also be taken into account if, for example, the imaged structure is the lens. In such a case, the plate 56 can be adjusted/configured so that the double pass of the plate 56 as well as the double pass of the cornea sum up to a polarization rotation of 90 degrees. Because the birefringence of the cornea may be different from patient to patient, the configuration/adjustment of the plate 56 can be done dynamically so as to optimize the signal returning to the detection sensor 54. Accordingly, the returning reflected portion of the beam 28 is now polarized to be at least partially reflected by the polarized beam splitter 48 so as to be directed through the filter 50, through the lens 51, and to the pinhole aperture 52. The filter 50 can be configured to block wavelengths other than the wavelengths of interest. The pinhole aperture 52 is configured to block any returning reflected portion of the beam 28 reflected from locations other than the focal point from reaching the detection sensor 54. Because the amount of returning reflected portion of the beam 28 that reaches the detection sensor 54 depends upon the nature of the tissue at the focal point of the beam 28, the signal generated by the detection sensor 54 can be processed in combination with data regarding the associated locations of the focal point so as to generate image/location data for structures of the eye.

In this embodiment, the same laser assembly may be used both for treatment (i.e., modification) and imaging of the target tissue. For instance, the target tissue may be imaged by raster scanning pulsed laser beam 28 along the target tissue to provide for a plurality of data points, each data point having a location and intensity associated with it for imaging of the target tissue. In some embodiments, the raster scan is selected to deliver a sparse pattern in order to limit the patient's exposure, while still discerning a reasonable map of the intraocular targets. In order to image the target tissue, the treatment laser beam (i.e. the laser beam having the parameters suitably chosen as described above for the modification of tissue) is preferably attenuated to the nano-Joule level for imaging of the structures to be treated. When used for imaging, the attenuated laser beam may be referred to as an imaging beam. In many embodiments, the treatment beam and the imaging beam may be the same except that the pulse energy of the laser source is lower than the treatment beam when the laser beam is used for imaging. In many embodiments, the pulse energy of the laser beam when used for imaging is preferably from about 0.1 nJ to 10 nJ, preferably less than 2 nJ and more preferably less than 1.8 nJ. The use of the same laser beam for both treatment and imaging provides for the most direct correlation between the position of the focal locations for imaging and treatment—they are the same beam. This attenuated probe beam can is preferably used directly in a back reflectance measuring configuration, but, alternatively, may be used indirectly in a fluorescence detection scheme. Since increases in both backscatter and fluorescence within tissue structures will be evident, both approaches have merit.

In a preferred embodiment, imaging of a first target area to be modified is performed sequentially with the modification of the tissue in the first target area before moving on to a second, different, target area, i.e. imaging is performed sequentially with treatment in a predetermined target area. Thus, for instance imaging of the lens capsule is preferably followed by treatment of the lens capsule before imaging is carried out on other either structures, such as the cornea or iris. In another embodiment, imaging of a first target area where a first incision to be place is performed sequentially with the scanning the treatment beam to perform the incision in the first target area before moving on to a second target area for performing a second incision, i.e. imaging of the area to be incised is performed sequentially with scanning the treatment beam to perform in the predetermined target area. In another embodiment, a cataract procedure comprises a capsulotomy incision, and at least one of a cataract incision and a limbal relaxing incision. In one embodiment, imaging of the target tissue where the capsulotomy is to be performed is followed by scanning of the treatment to perform the capsulotomy, and then the treatment beam is scanned to perform the capsulotomy. Subsequently, imaging of the target tissue where the at least one of the cataract incisions (CI) and the limbal relaxing incision (LRI) is carried out and then the treatment beam is scanned to perform the at least one of the LRI and the CI. When an LRI is selected, this minimizes the chance for the patient to move between imaging and treatment for the LRIs which are the most critical/sensitive to eye movements between image and treatment.

As shown in the illustrated embodiment, the scanning assembly 18 can include a z-scan device 58 and a xy-scan device 60. The z-scan device 58 is operable to vary a convergence/divergence angle of the beam 28 and thereby change a location of the focal point in the direction of propagation of the beam 28. For example, the z-scan device 58 can include one or more lenses that are controllably movable in the direction of propagation of the beam 28 to vary a convergence/divergence angle of the beam 28. The xy-scan device 60 is operable to deflect the beam 28 in two dimensions transverse to the direction of propagation of the beam 28. For example, the xy-scan device 60 can include one or more mirrors that are controllably deflectable to scan the beam 28 in two dimensions transverse to the direction of propagation of the beam 28. Accordingly, the combination of the z-scan device 58 and the xy-scan device 60 can be operated to controllably scan the focal point in three dimensions, for example, within the eye of the patient.

As shown in the illustrated embodiment, a camera 62 and associated video illumination 64 can be integrated with the scanning assembly 18. The camera 62 and the beam 28 share a common optical path through the objective lens assembly 20 to the eye. A video dichroic 66 is used to combine/separate the beam 28 with/from the illumination wavelengths used by the camera. For example, the beam 28 can have a wavelength of about 355 nm and the video illumination 64 can be configured to emit illumination having wavelengths greater than 450 nm. Accordingly, the video dichroic 66 can be configured to reflect the 355 nm wavelength while transmitting wavelengths greater than 450 nm.

Figure 3:
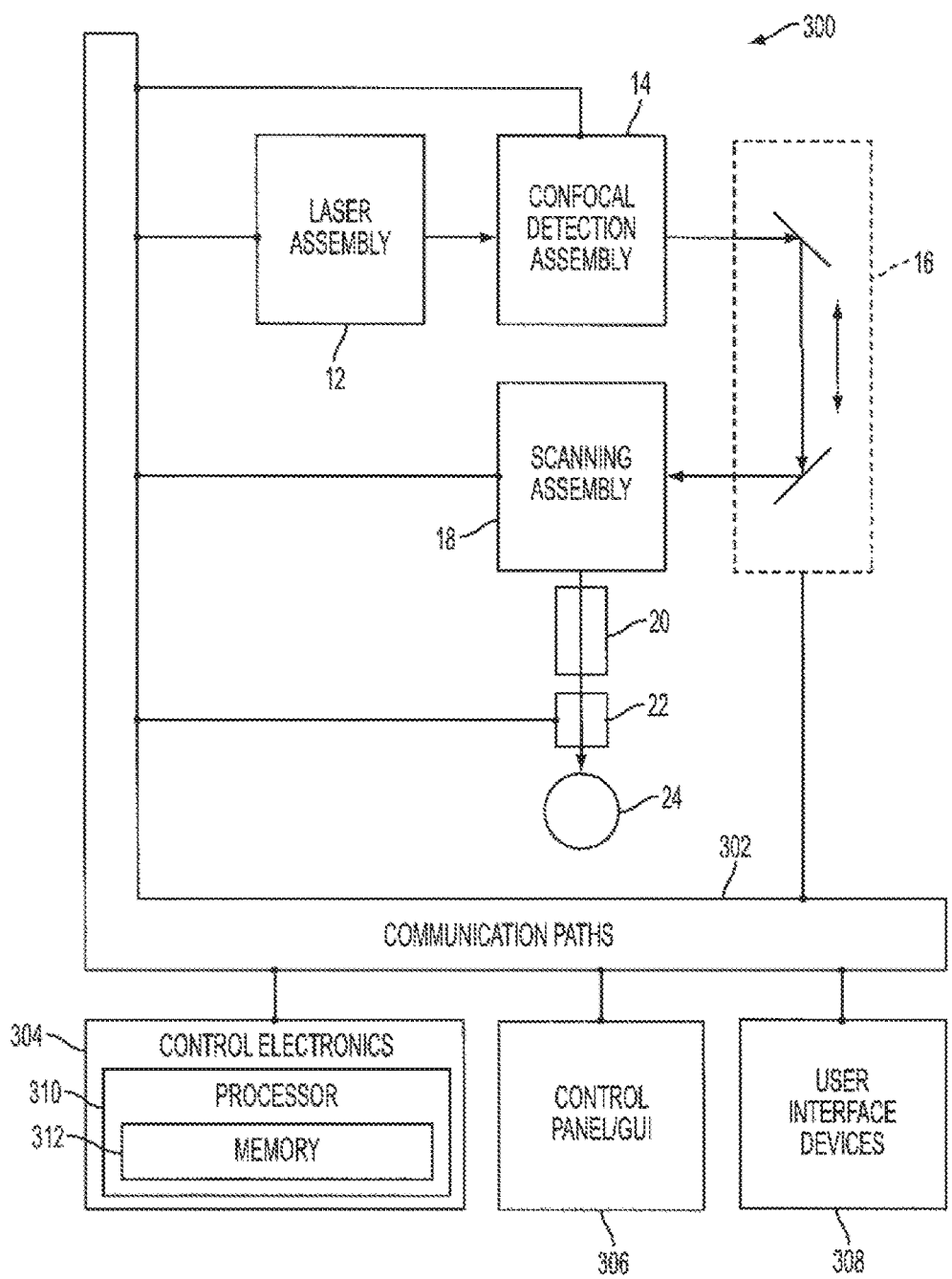
FIG. 3 is a schematic diagram of an embodiment of the laser surgery system of FIG. 1.

FIG. 3 schematically illustrates a laser surgery system 300 according to many embodiments. The laser surgery system 300 includes the laser assembly 12, the confocal detection assembly 14, the shared optics 16, the scanning assembly 18, the objective lens assembly 20, the patient interface 22, communication paths 302, control electronics 304, control panel/graphical user interface (GUI) 306, and user interface devices 308. The control electronics 304 includes processor 310, which includes memory 312. The patient interface 22 is configured to interface with a patient 24. The control electronics 304 is operatively coupled via the communication paths 302 with the laser assembly 12, the confocal detection assembly 14, the shared optics 16, the scanning assembly 18, the control panel/GUI 306, and the user interface devices 308.

The scanning assembly 18 can include a z-scan device and a xy-scan device. The laser surgery system 300 can be configured to focus the electromagnetic radiation beam 28 to a focal point that is scanned in three dimensions. The z-scan device can be operable to vary the location of the focal point in the direction of propagation of the beam 28. The xy-scan device can be operable to scan the location of the focal point in two dimensions transverse to the direction of propagation of the beam 28. Accordingly, the combination of the z-scan device and the xy-scan device can be operated to controllably scan the focal point of the beam in three dimensions, including within a tissue of the patient 24 such as within an eye tissue of the patient 24. The scanning assembly 18 is supported by the shared optics 16, which may be configured to accommodate patient movement induced movement of the scanning assembly 18 relative to the laser assembly 12 and the confocal detection assembly 14 in three dimensions. The patient interface 22 is coupled to the patient 24 such that the patient interface 22, the objective lens assembly 20, and the scanning assembly 18 move in conjunction with the patient 24. For example, in many embodiments, the patient interface 22 employs a suction ring that is vacuum attached to an eye of the patient 24. The suction ring can be coupled with the patient interface 22, for example, using vacuum to secure the suction ring to the patient interface 22.

The control electronics 304 controls the operation of and/or can receive input from the laser assembly 12, the confocal detection assembly 14, the free-floating assembly 16, the scanning assembly 18, the patient interface 22, the control panel/GUI 306, and the user The interface devices 308 via the communication paths 302. The communication paths 302 can be implemented in any suitable configuration, including any suitable shared or dedicated communication paths between the control electronics 304 and the respective system components. The control electronics 304 can include any suitable components, such as one or more processors, one or more field-programmable gate arrays (FPGA), and one or more memory storage devices. In many embodiments, the control electronics 304 controls the control panel/GUI 306 to provide for pre-procedure planning according to user specified treatment parameters as well as to provide user control over the laser eye surgery procedure.

The control electronics 304 can include a processor/controller 310 that is used to perform calculations related to system operation and provide control signals to the various system elements. A computer readable medium 312 is coupled to the processor 310 in order to store data used by the processor and other system elements. The processor 310 interacts with the other components of the system as described more fully throughout the present specification. In an embodiment, the memory 312 can include a look up table that can be utilized to control one or more components of the laser system surgery system 300. The processor 310 can be a general purpose microprocessor configured to execute instructions and data, such as a Pentium processor manufactured by the Intel Corporation of Santa Clara, Calif. It can also be an Application Specific Integrated Circuit (ASIC) that embodies at least part of the instructions for performing the method according to the embodiments of the present disclosure in software, firmware and/or hardware. As an example, such processors include dedicated circuitry, ASICs, combinatorial logic, other programmable processors, combinations thereof, and the like memory 312 can be local or distributed as appropriate to the particular application. Memory 312 can include a number of memories including a main random access memory (RAM) for storage of instructions and data during program execution and a read only memory (ROM) in which fixed instructions are stored. Thus, the memory 312 provides persistent (non-volatile) storage for program and data files, and may include a hard disk drive, flash memory, a floppy disk drive along with associated removable media, a Compact Disk Read Only Memory (CD-ROM) drive, an optical drive, removable media cartridges, and other like storage media.

The user interface devices 308 can include any suitable user input device suitable to provide user input to the control electronics 304. For example, the user interface devices 308 can include devices such as, for example, a touch-screen display/input device, a keyboard, a footswitch, a keypad, a patient interface radio frequency identification (RFID) reader, an emergency stop button, and a key switch.

Figure 4:
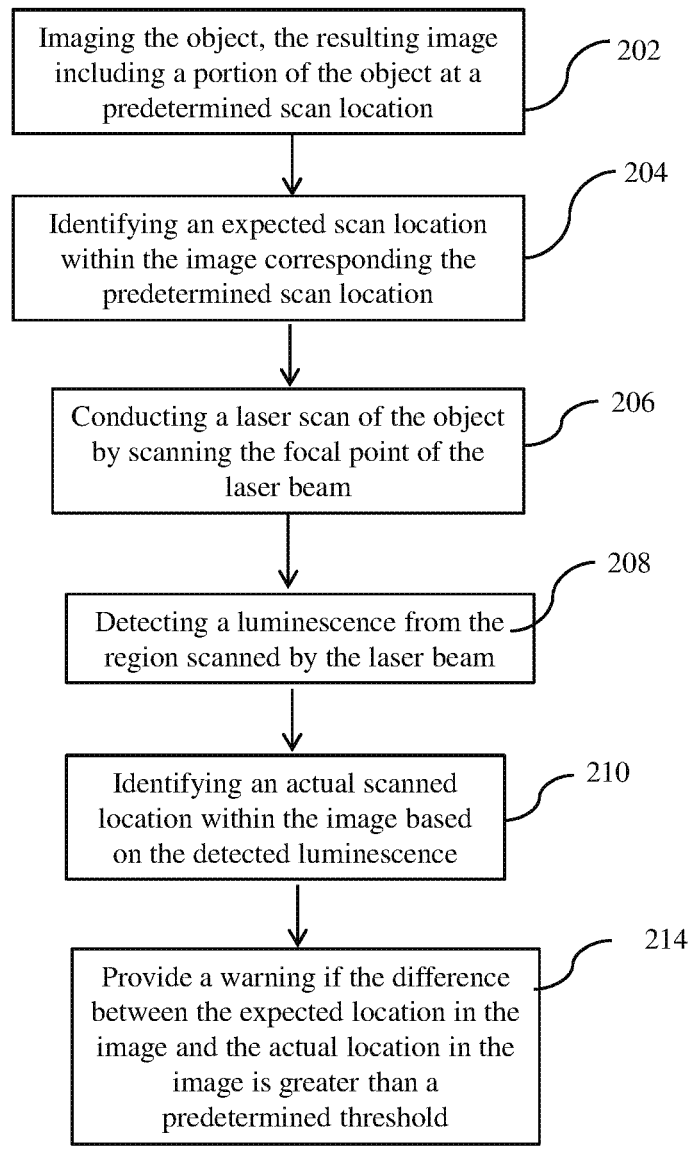
FIG. 4 is a block diagram illustrating several acts of the methods and acts for laser scan verification in many embodiments.

Certain acts or steps in connection with the methods and systems of verifying the location of a laser scan in an object, preferably an eye are shown in FIG. 4. In some embodiments, the object is an eye and the methods and acts of verifying the locations of the laser scan is operable to verify the location of an incision in ocular surgical procedures, including cataract surgery. In other embodiments, the object is a calibration apparatus, and the methods and acts are operable to verify the calibration of a laser surgical system, preferably a laser eye surgical system.

Figure 5:
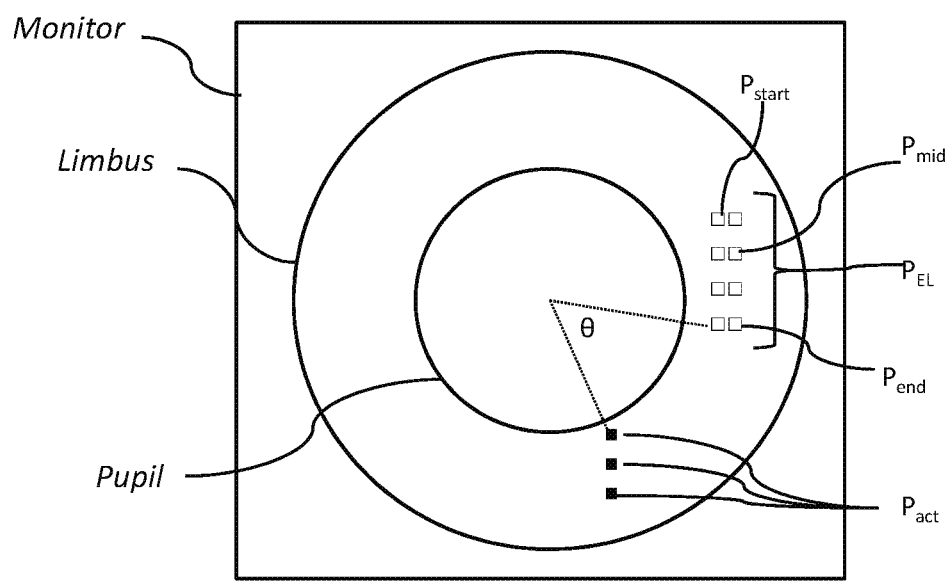
FIG. 5 illustrates an en face image of an eye.

The methods and/or acts of verifying the location of a laser scan within an object include, at Step 202 (FIG. 4), imaging the object, the resulting image including a portion of the object at a predetermined location to be scanned. The type or manner of imaging is not particularly limited, so long as the selected imaging method is capable of imaging the portion of the object in which the predetermined scan location is located. In many embodiments, the predetermined scan location includes the location of an incision that has been prescribed or identified by a health professional for placement in a tissue of the eye, such as the lens capsule, the lens, the cornea or the limbus. In this case, the selected imaging method should be capable of imaging the selected tissue. In one embodiment, the imaging method is optical imaging by a camera, and the image is presented as an en face image of the eye on monitor as shown in FIG. 5. The image may likewise be a video image in which successive images are captured in real time by a sensor and displayed on a monitor. The monitor may operate at, for instance, 60 Hz, 120 Hz or 240 Hz.

In another embodiment, the imaging method includes scanning the location of a focal point of a pulsed laser beam and confocally detecting light reflected from the location of the pulsed laser. Preferably, the pulsed laser beam is an ultraviolet pulsed laser beam having a wavelength of 320-370 nm. In many embodiments, the methods of verifying the location of a laser scan within an object include both video imaging and confocal imaging.

The methods and/or acts of verifying the location of a laser scan within an object include, at Step 204, identifying an expected scan location within the image corresponding to the predetermined scan location. In many embodiments, a camera 62 in the imaging system includes a sensor having an orthogonal array of pixels (e.g., in x and y directions where the corresponding z direction is in the direction of propagation of the electromagnetic radiation beam). Thus, in many embodiments, the image is comprised of an array of pixels, preferably color pixels. In many embodiments, a calibration of the system, according to the methods described herein, provide a known relationship between the location of a pixel in the orthogonal array of the image and a location of the tissue in the treatment space. This known correspondence between the pixels in the image and a location in treatment space makes it possible to identify an expected scan location in the image corresponding to the predetermined scan location. In many embodiments, the expected scan location within the image is a set of pixels, PEL illustrated visually in FIG. 5 (not to scale), that is a subset of the array of pixels comprising the image. The set of pixels, PEL, may include a pixel denominated as an expected starting point pixel of the expected scan location, Pstart, a pixel may be identified as an expected ending point pixel, Pend, of the expected scan location or a pixel denominated as a midpoint pixel, Pmid, located at some position between the starting point pixel and the ending point pixel.

The methods and/or acts of verifying the location of a laser scan within an object include, at Step 206, conducting a laser scan of the object by scanning a focal point of the laser beam through at least a portion of the object. The location of the scan is not particularly limited; however, in many embodiments, it will preferably include the predetermined scan location. The laser beam is preferably a pulsed laser beam, and preferably a pulsed ultraviolet laser beam. The laser scan is preferably a raster scan of the pulsed laser beam. In some embodiments, the laser beam may be of sufficient energy to modify the eye tissue scanned, and such that a succession of laser pulses within the eye tissue is sufficient to incise the tissue scanned. In other embodiments, the energy of the laser beam will be insufficient to modify the tissue scanned. The intensity of the laser beam is also preferably insufficient to cause the formation of a plasma, and also preferably insufficient to generate one or more cavitation events, such as the formation of a bubble.

The methods and/or acts of verifying the location of a laser scan within an object include, at Step 208, detecting the luminescence region scanned by the laser beam. As would be understood by those ordinarily skilled, individual photons of the ultraviolet laser beam, each having an energy, hv, will be absorbed by various components in the tissue scanned. This absorbed light will then be re-emitted by the component as a photon of lower energy (larger wavelength) either by fluorescence or phosphorescence from the scanned tissue. When ultraviolet light is used for the laser scan, the emitted luminescence generally includes light in the blue, indigo and violet portions of the visible spectrum, having wavelengths from about 400 nm to 475 nm. The emission of light from tissue, including by processes such as fluorescence or phosphorescence, is generally referred to herein as luminescence. In many embodiments, the luminescence, preferably in the range of 400 nm to 475 nm light is detected using the same camera 62 and same sensor having the orthogonal array of pixels which was used to image an object.

The methods and/or acts of verifying the location of a laser scan within an object include, at Step 208, detecting the luminescence from the region scanned by the laser beam. As would be understood by those ordinarily skilled, each pixel has red (R), Green (G) and Blue (B) components ("R, G, B components"), each having an intensity, I, associated with it that has a value from Imin to Imax. In many embodiments, Imin=0 and Imax=255. According to some embodiments, the actual scanned location within the image may be determined monitoring the intensity, IB, of the B component of the pixels that make up the image. In many embodiments, the actual scanned location may be comprised of one or more Pixels, Pact in the image. In many embodiments, a pixel, Pact, is identified as being an actual scanned location if the measured value of Ib for the pixel is greater than a predetermined threshold value, Ip. More than one Pact may be identified in one image or frame. The predetermined threshold value may be empirically determined based on the object to be imaged. For instance, if the object to be imaged contains very few blue components, it may be possible to determine luminescence based on a relatively small Ib. In contrast, if the object to be imaged contains a relatively large amount of blue components, it may be necessary to determine luminescence based on a relatively large IB. Those skilled in the art thus instructed can suitably determine the necessary threshold for each application. In some embodiments, the predetermined threshold value, Ip, may be 0.9Imax, 0.8Imax, 0.7Imax, 0.6Imax, 0.5Imax, 0.4Imax, 0.3Imax, 0.2Imax, or 0.1Imax. This may be termed a "pixel thresholding" approach.

In other embodiments, the actual scanned location within the image may be determined by comparing the intensity, IB, of the B component of a pixel in successive images or frames an image. In this embodiment, the actual scanned location is determined by calculating a difference between an Ib value of a pixel in a first frame, Ib1, and the Ib value of the same pixel in a second successive frame, Ib2. In many embodiments, a pixel is identified as being an actual scanned location if the measured value difference, Ib2−Ib1 for a pixel is greater than a predetermined threshold value, IP. The predetermined threshold value may be empirically determined based on the object to be imaged; however, since the identification is based on a difference in the same pixel in successive frames, the threshold may not be as sensitive to the amount of blue in the components of the image. In some embodiments, the predetermined threshold value, Ip, may be 0.9Imax, 0.8Imax, 0.7Imax, 0.6Imax, 0.5Imax, 0.4Imax, 0.3Imax, 0.2Imax, or 0.1Imax. This may be termed a "consecutive differential" approach.

In other embodiments, the actual scanned location within the image may be determined by comparing an intensity, IB, of the B component of a pixel in a first frame or image and then calculating a difference in intensity value for the pixel in each successive image or frame compared to its intensity of the first frame. In this embodiment, the actual scanned location is determined by comparing an Ib value of a pixel in a first frame, Ib1, with the Ib value of the same pixel in each successive i=2, n frames, i.e. Ib2 Ib3, Ib4 . . . Ibn etc. In many embodiments, a pixel is identified as being an actual scanned location if the measured value difference, Ibi−Ib1 for a pixel is greater than a predetermined threshold value, IP. The predetermined threshold value may be empirically determined based on the object to be imaged; however, since the identification is based on a difference in the same pixel in successive frames, the threshold may not be as sensitive to the amount of blue in the components of the image. In some embodiments, the predetermined threshold value, Ip, may be 0.9Imax, 0.8Imax, 0.7Imax, 0.6Imax, 0.5Imax, 0.4Imax, 0.3Imax, 0.2Imax, or 0.1Imax. This may be termed an "absolute differential" approach.

In some embodiments, a statistical approach may be implemented for determining the actual scanned location within the image. In these probabilistic approaches, the values for the intensity, IB of the thresholding approach, the value of Ib2−Ib1 in the consecutive differential approach and the value Ibi−Ib1 in the absolute differential is assigned a probability of being an actual scanned location, and is determined to be an actual scanned location if the value of the probability is greater than a predetermined probability, for instance 50% (i.e., 0.5), or 60%, 70%, 80% or 90%.

Since a scan is conducted over a period of time, the pixels which are identified as being an actual scanned location, Pact, may change during the time course of the scan. Analysis, such as by overlaying successive frames or obtaining difference images between frames, either of individual pairs of frames or of all successive images/frames during the scan permits the determination of all the actual scanned locations and of the direction of the scan during the scan. In some embodiments, all actual scanned locations may be determined before a comparison of the actual scanned location with the expected scan location is completed.

The methods and/or acts of verifying the location of a laser scan within an object include, at Step 214, providing a warning if a difference between the actual location in the image and an expected scan location in the image is greater than a threshold distance, DT. The nature of the warning is not particularly limited. For instance, a warning message may be placed on the image indicating a difference in the expected scan location and actual scan location has been detected. The warning may optionally include stopping the scan and alerting a user. Where the object is an eye, the warning may also optionally include reducing the intensity of the laser beam below a level necessary to incise the tissue.

The manner of calculating the difference between the expected scan location and the actual scan location is not particularly limited. In many embodiments, the calculated difference may be a distance between the expected scan location and the actual scanned location. The distance may be between any of the one or more pixels, Pact, identified as an actual scan location and any pixel from the set of pixels, PEL, which comprises the expected scan locations. In some embodiments, one Pact from the actual scan locations is selected for the distance measurement and one pixel is selected from the set of PEL pixels for the distance measurements. In some embodiments, the selected expected scan location pixel may be either Pstart, Pend or a Pmid. The distance may be calculated as a number of pixels separating the selected pixels. Alternatively, the distance may be calculated as a physical distance in, for instance, units of microns. In another alternative, it may be suitable to calculate the distance as an angular distance between the pixels, for instance, by an angle theta, $\theta$, around an axis centered at the pupil center in the direction of propagation of the laser light source. The threshold difference, DT, may be chosen based on the units selected. In the case of a distance measured in microns, the threshold difference DT, may be 5000 microns, or 1000 microns, or 500 microns or 200 microns or 100 microns, or 50 microns or 5 microns. In the case of angular distance, the distance DT, may be 120°, or 90°, or 60°, or 45°, or 30°, or 15°.

The methods and/or acts of verifying the location of a laser scan may be used in connection with laser eye surgery systems and methods to verify the placement of one or more ocular incisions, including in methods for cataract surgery using a laser eye surgery system for verifying the placement of incisions in a cataract surgery. The laser eye surgery system may be the one shown in FIGS. 1-3 and described herein. Thus, some embodiments are a laser surgical system configured to carry out the methods described herein. In some embodiments, a user or physician will define one or more incisions to be performed by the laser surgical system during cataract surgery selected from capsulotomy incisions, primary incisions, sideport incisions and arcuate incisions by entering the necessary parameters into system to define the incision. The laser surgical system is configured to receive those parameters, image the eye, identify the expected scan location within the image corresponding to the selected incisions, conduct a laser scan of the eye by scanning the focal point of a laser beam, detect luminescence from the region scanned, identify the actual scanned location within the image based on the detected luminescence, and provide a warning to the user if the difference between the expect location in the image and the actual location in the image is greater than a predetermined threshold. In some embodiments, the laser scan that is conducted is a confocal imaging scan of the eye to verify that the confocal imaging scan is imaging the actual location to be incised. In some embodiment, the laser scan conducted is a treatment scan of sufficient energy to incise the tissue to be treated. In other embodiments, the scan conducted is the same as the treatment scan but at energies insufficient to incise human tissue. This scan can be done in order to verify the placement of the incisions prior to conducting a treatment scan capable of incising tissue.

Figure 6A:
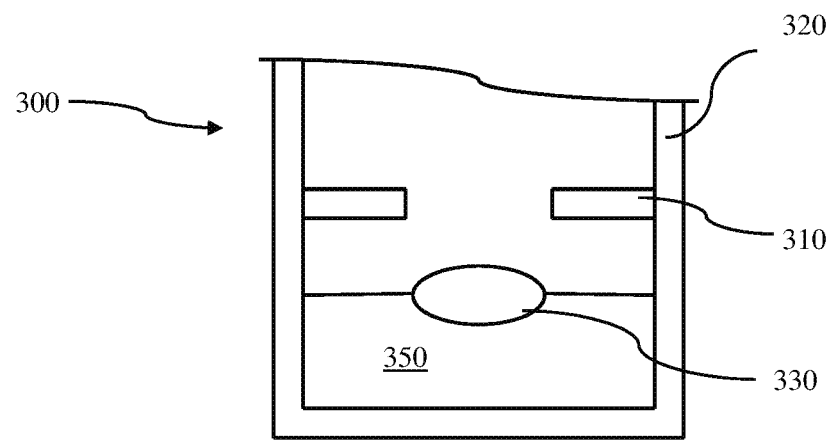
FIGS. 6A and 6B illustrate a calibration apparatus.
Figure 6B:
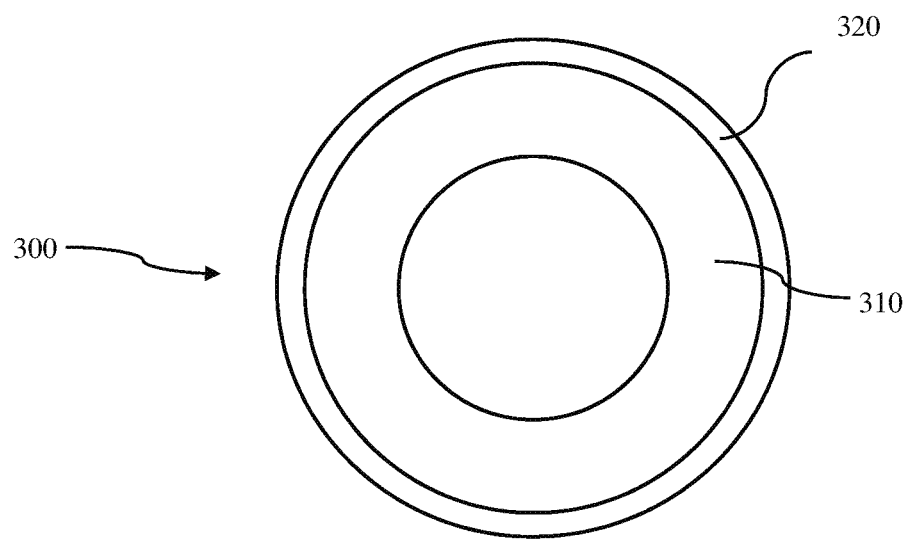

The methods and/or acts of verifying the location of a laser scan may be used in connection with laser eye surgery systems and methods to verify the calibration of an eye surgical system prior to treatment. The methods or acts of verifying the calibration may include a calibration apparatus 300 shown in FIGS. 6A and 6B. The calibration apparatus 300 includes sidewall 320 and also comprises structures similar to structures of an eye. For example, the calibration apparatus 300 may include a container 350 having a viscous substance or solid substance that is similarly optically transmissive to the structures of the eye. The material 350 may comprise of visco-elastic fluid, a gel or other optically transmissive structure and material, for example. The calibration apparatus 300 comprises an iris structure 310 and, optionally, a lens structure 330, either of which can provide a suitable surface for calibration. At least one of the surfaces of lens structure 330 or iris structure 310 should emit blue wavelength light when irradiated by ultraviolet light. Here, a structure or property is "similar" if it is within 10%, preferably within 5% and more preferably within about 1% of a typical measurement of that structure or property in an adult human eye. The calibration structure 300 may connect to the patient interface as described herein and a fluid (note shown) can be provided above the calibration apparatus, for example.

A method and/or acts of verifying the calibration of laser surgical system, including a laser eye surgical system, include imaging a calibration apparatus, identifying an expected scan location within the image corresponding to a predetermined scan pattern within the calibration apparatus, conducting a laser scan of the calibration apparatus by scanning the focal point of a laser beam, detecting luminescence from the region of the calibration area scanned, identifying the actual scanned location within the image based on the detected luminescence, and identifying the laser surgical system as not calibrated if a difference between the expected scan location in the image and the actual location in the image is greater than a predetermined threshold. The method can also include identifying the laser surgical system as calibrated if a difference between the expected scan location in the image and the actual location in the image is less than a predetermined threshold.

System Calibration

In many embodiments, a calibration of the system is carried out to provide a known relationship between the location of a pixel in the orthogonal array of the image and a location of the tissue in the treatment space. This known correspondence between the pixels in the image and a location in treatment space makes it possible to identify an expected scan location in the image corresponding to the predetermined scan location, an actual scanned location of a laser scan in the image and a difference between the actual scanned location and the expected scan location. The method for performing the calibration is not particularly limited. Examples of suitable calibration methods can be found, for instance, in U.S. patent application Ser. No. 14/069,703, filed Nov. 1, 2013, entitled "Laser Surgery System Calibration," and U.S. patent application Ser. No. 14/191,095, filed Feb. 26, 2014, the entire contents of which are hereby incorporated by reference herein in its entirety.

In brief, the laser surgery system 10 can be calibrated to relate locations in a treatment space with pixels in the camera 62 and with control parameters used to control the scanning assembly 18 such that the focal point of the electromagnetic radiation beam can be accurately positioned within the intraocular target. Such calibration can be accomplished at any suitable time, for example, prior to using the laser surgery system 10 to treat a patient's eye.

FIG. 7A is a top view diagram of a calibration plate 402 that can be used to calibrate the laser surgery system 10. In many embodiments, the calibration plate 402 is a thin plate having an array of target features, for example, through holes 404 therein. In alternate embodiments, the calibration plate 402 is a thin plate having a field of small dots as the target features. While any suitable arrangement of the target features can be used, the calibration plate 402 of FIG. 7A has an orthogonal array of through holes 404. Any suitable number of the target features can be included in the calibration plate 402. For example, the illustrated embodiment has 29 rows and 29 columns of the through holes 404, with three through holes at each of the four corners of the calibration plate 402 being omitted from the orthogonal array of through holes 404.

In many embodiments, each of the through holes 404 is sized small enough to block a suitable portion of an electromagnetic radiation beam when the focal point of the electromagnetic radiation beam is not located at the through hole. For example, each of the through holes 404 can have a diameter slightly greater than the diameter of the focal point of the electromagnetic radiation beam so as to not block any of the electromagnetic radiation beam when the focal point is positioned at one of the through holes 404. In the embodiment shown, the through holes 404 have a diameter of 5 μm, which is sized to be used in conjunction with a focal point diameter of 1 μm.

FIG. 7B schematically illustrates using the calibration plate 402 to calibrate the camera 62 of the laser surgery system 10. The calibration plate 402 is supported at a known fixed location relative to the objective lens assembly 20. In many embodiments, the objective lens assembly 20 is configured for telecentric scanning of the electromagnetic radiation beam and the calibration plate 402 is supported to be perpendicular to the direction of propagation of the electromagnetic radiation beam. The calibration plate 402 is disposed between the objective lens assembly 20 and a light source 406. The light source 406 is used to illuminate the calibration plate 402. A portion of the illumination light from the light source 406 passes through each of the through holes 404, thereby producing an illuminated location within the field of view of the camera 62 at each of the through holes 404. A light beam 408 from each of the through holes 404 passes through the objective lens assembly 20, through the video dichroic 66, an into the camera 62. In many embodiments, the camera 62 includes a sensor having an orthogonal array of pixels (e.g., in x and y directions where the corresponding z direction is in the direction of propagation of the electromagnetic radiation beam). In many embodiments, X and Y pixel values for each of the light beams 408 is used in conjunction with the known locations of the through holes 404 relative to the objective lens assembly 20 to determine the relationship between the camera X and Y pixel values and locations in the treatment space for dimensions transverse to the propagation direction of the electromagnetic radiation beam.

FIG. 7C schematically illustrates using the calibration plate 402 to calibrate the scanning assembly 18. The calibration plate 402 is supported at a known fixed location relative to the objective lens assembly 20. In many embodiments, the objective lens assembly 20 is configured for telecentric scanning of the electromagnetic radiation beam and the calibration plate 402 is supported to be perpendicular to the direction of propagation of the electromagnetic radiation beam. The calibration plate 402 is disposed between the objective lens assembly 20 and a detector 410. The detector 410 is configured to generate a signal indicative of how much of the electromagnetic radiation beam is incident thereon, thereby being indirectly indicative of how much of the electromagnetic radiation beam is blocked by the calibration plate 402. For example, when the focal point of the electromagnetic radiation beam is positioned at one of the through holes 404 (as illustrated for the focal point disposed on the right side of the detection plate 402 in FIG. 7B), a maximum amount of the electromagnetic radiation beam passes through the through hole and is incident on the detector 410. In contrast, when the focal point of the electromagnetic radiation beam is not positioned at one of the through holes 404 (as illustrated for the focal point disposed above the left side of the detection plate 402 in, a portion of the electromagnetic radiation beam is blocked from reaching the detector 410.

Control parameters for the z-scan device 58 and the xy scan device 60 are varied to locate the focal point of the electromagnetic radiation beam at each of a suitable set of the through holes, thereby providing data used to determine the relationship between the control parameters for the scanning assembly 18 and the resulting location of the focal point of the electromagnetic radiation beam. The z-scan device 58 is operable to vary a convergence/divergence angle of the electromagnetic radiation beam, thereby being operable to control the distance of the focal point from the objective lens in the direction of propagation of the electromagnetic radiation beam. The xy-scan device 60 is operable to vary a direction of the electromagnetic radiation beam in two dimensions, thereby providing the ability to move the focal point in two dimensions transverse to the direction of propagation of the electromagnetic radiation beam.

A suitable existing search algorithm can be employed to vary the control parameters for the z-scan device 58 and the xy-scan device 60 so as to reposition the focal point to be located at each of a suitable set of the through holes 404. In many embodiments where the objective lens assembly 20 is configured to telecentrically scan the electromagnetic radiation beam, the resulting control parameter data for the scanning assembly 18 can be used to calibrate the scanning assembly 18 relative to directions transverse to the direction of propagation of the electromagnetic radiation beam (e.g., x and y directions transverse to a z direction of propagation of the electromagnetic radiation beam).

Application to Cataract Surgery

In many embodiments, the methods and/or acts of verifying the location of a laser scan is used with laser eye surgery systems and methods to verify the placement of one or more ocular incisions. In many embodiments, the methods and/or acts are used in cataract surgery using a laser eye surgery system for verifying the placement of incisions in a cataract surgery.

In cataract surgery, a capsulotomy incision, often in the form of a small round hole is formed in the anterior side of the lens capsule to provide access to the lens nucleus.

In addition, cataract surgery may include three types of cornea incisions: arcuates, primaries and sideports. Parameters that may be used to define the capsulotomy include shape (i.e. circular, elliptical, rectangular or polygonal) and size. The systems described herein are designed to receive these parameters based on user or physician's input and preferably, to provide a prompt for their input where not received.

Primary incisions and sideport incisions may have the same structure. They are generally multiplanar structures that create an opening that allow the physician access into the anterior chamber. The primaries are used for insertion of the aspiration tool and the insertion of the IOL. Sideport incisions may be used for inserting smaller instrumentation into the anterior chamber. The location and shape of both the primary incisions and the sideport incisions are determined by the user parameters and, optionally, by information from a section scan as described herein, where the cornea anterior and posterior surfaces may be modeled by circles. The anterior and posterior curvatures of the cornea as measured in the circular fits of the section scans may optionally be used to position the cuts. Parameters that may be used to define the primary cataract incision or the sideport incision are preferably selected from the group consisting of limbus offset, width, side cut angle, plane depth and length. The systems described herein are designed to receive these parameters based on user or physician's input and preferably, to provide a prompt for their input where they are not received.

Arcuate incisions may be used to correct a patient's astigmatism. For instance, they may adjust the curvature of the cornea to a more spherical shape by means relaxing stresses along the meridian on which they are placed. They are parts of a conical surface that crosses both the anterior and posterior surfaces of the cornea. In some embodiments, the anterior curvature and posterior curvature of the cornea, as measured in a circular fit to a section scan, are used to position an "along-the-cut" scan. The along-the-cut scan lays on the surface of a cone that transverses the cornea. The arcuate incision can be located within the along-the-cut scan. Parameter that may be used to define the arcuate incision may include the size of the optical zone, arc length, uncut anterior portion, uncut posterior portion and side cut angle. The systems described herein are designed to receive these parameters based on user or physician's input and preferably, to provide a prompt for their input where not received.

Capsulotomy Incisions

The laser surgery system 10 can be used to form any suitably shaped capsulotomy. For example, while the anterior and posterior capsulotomies in the illustrated embodiments are circular, any other suitable shape, including but not limited to, elliptical, rectangular, and polygonal can be formed. And the anterior and/or posterior capsulotomy can be shaped to accommodate any correspondingly suitably shaped IOL.

Figure 8:
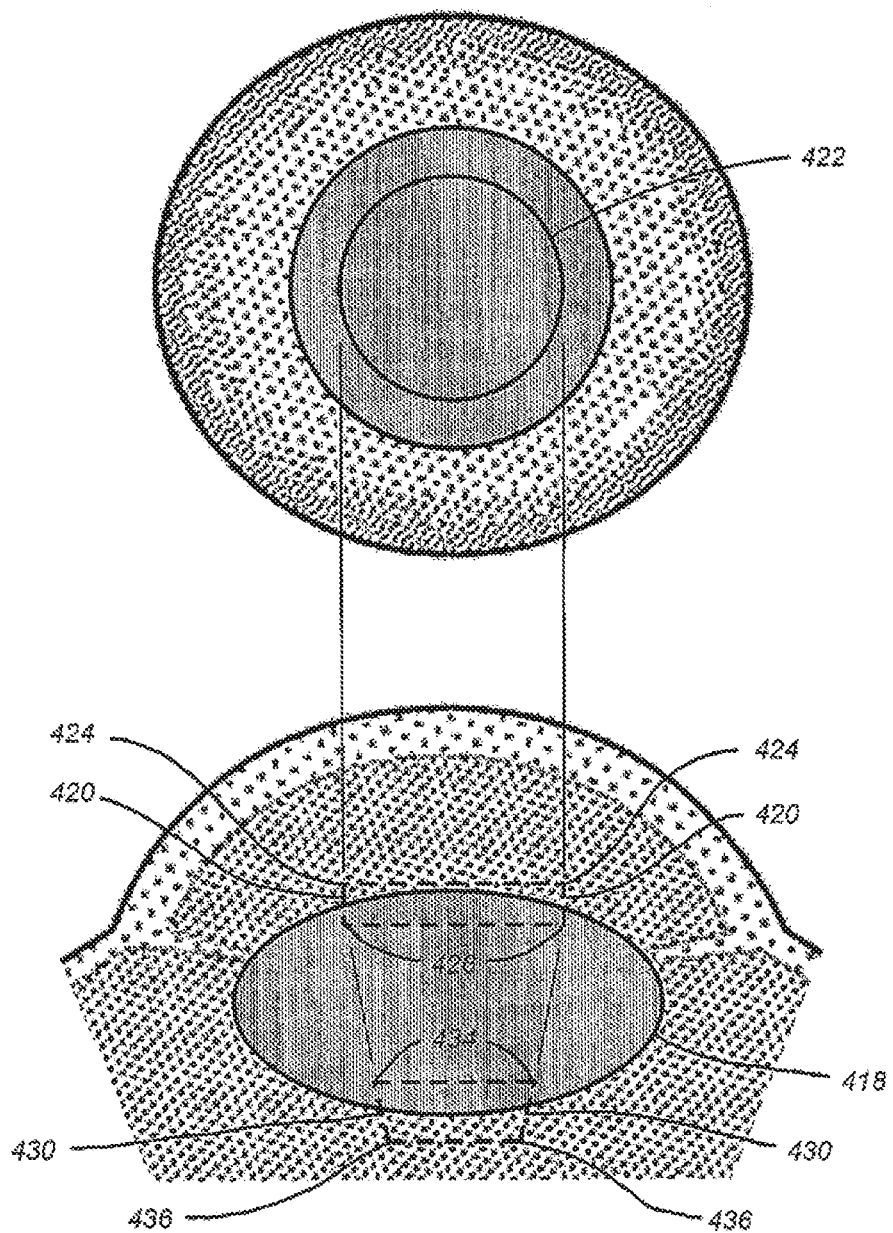
FIG. 8 shows a plan view of a capsulotomy incision locator and a cross-sectional view showing projection of the capsulotomy incision locator on the lens anterior capsule according to many embodiments.

For example, referring now to FIG. 8, the laser surgery system 10 can be used to incise an anterior capsulotomy and/or a posterior capsulotomy in the anterior portion of a lens capsule 418. The focal point of the electromagnetic radiation beam can be scanned to form an anterior capsulotomy closed incision boundary surface 420 that transects the anterior portion of the lens capsule 418. Likewise, the focal point of the electromagnetic radiation beam can be scanned to form a posterior capsulotomy closed incision boundary surface 430 that transects the posterior portion of the lens capsule 418.

The anterior and/or posterior closed incision boundary surfaces 420, 430 can be designated using any suitable approach. For example, a plan view of the patient's eye can be obtained using the camera 62. A capsulotomy incision designator 422 can be located and shown superimposed on the plan view of the patient's eye to illustrate the size, location, and shape of a planned capsulotomy relative to the patient's eye. The capsulotomy incision designator 422 can be manually defined by an operator of the laser surgery system 10 and/or the laser surgery system 10 can be configured to generate an initial capsulotomy incision designator 422 for operator verification and/or modification.

The anterior capsulotomy closed incision boundary surface 420 can be defined on a projection of the capsulotomy incision designator 422 such that the anterior capsulotomy closed incision boundary surface 420 transects the anterior portion of the lens capsule 418 at all locations around the anterior capsulotomy incision boundary surface 420 for all expected variations in the location of the anterior portion of the lens capsule 418 relative to the projection of the capsulotomy incision designator 422. For example, a curve corresponding to the capsulotomy incision designator 422 can be projected to define an intersection with a minimum depth mathematical surface model (e.g., a spherical surface) defining a minimum expected depth configuration for the anterior portion of the lens capsule 418 with the resulting intersection being an anterior capsulotomy upper closed curve 424 that defines an upper boundary for the anterior capsulotomy closed incision boundary surface 420. Likewise, the curve corresponding to the capsulotomy incision designator 422 can be projected to define an intersection with a maximum depth mathematical surface model (e.g., a spherical surface) defining a maximum expected depth configuration for the anterior portion of the lens capsule 418 with the resulting intersection being an anterior capsulotomy lower closed curve 426 that defines a lower boundary for the anterior capsulotomy closed incision boundary surface 420. Alternatively, the focal point can be scanned using a low imaging-only power level (e.g., a power level sufficient to provide for imaging of the intraocular target via processing of the signal generated by the detection sensor 54 of the confocal detection assembly 14 without modifying the intraocular target) along the projection of the capsulotomy incision designator 422 while varying the depth of the focal point to determine the depth of the anterior lens capsule at a sufficient number of locations around the projection of the capsulotomy incision designator 422. The measured depths of the anterior lens capsule can then be used to determine suitable anterior capsulotomy upper and lower boundary curves 424, 426 of the anterior capsulotomy closed incision boundary surface 420.

Corneal Incisions

The laser surgery system 10 can be used to form any suitably shaped arcuate, primary, or sideport incisions.

Figure 9A:
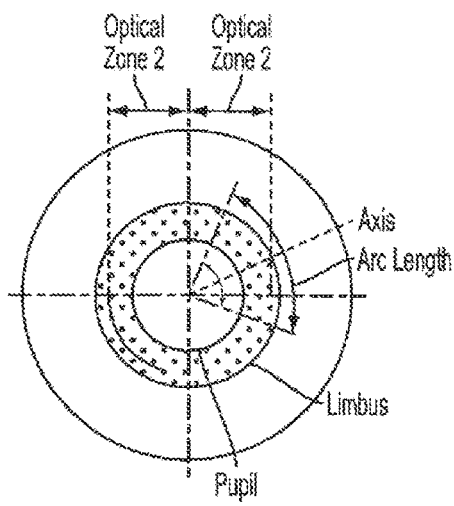
FIGS. 9A, 9B and 9C illustrate aspects of arcuate incisions of a cornea that can be formed by the laser surgery system of FIG. 1 according to many embodiments.
Figure 9B:
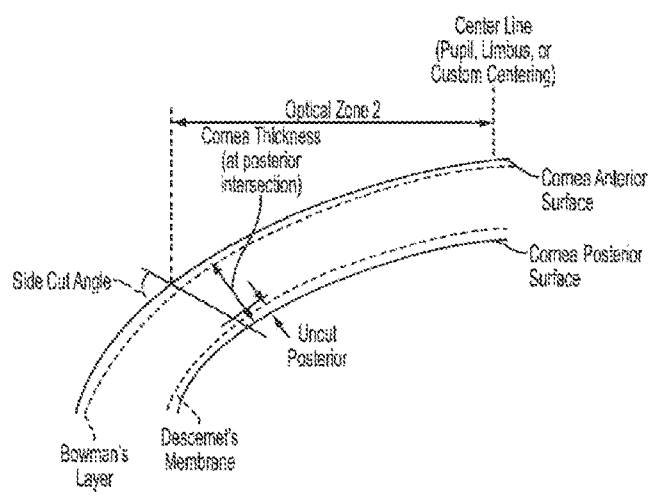
Figure 9C:
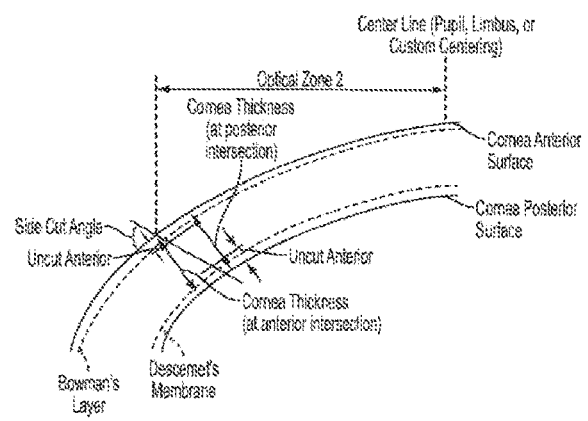

FIGS. 9A through 9C illustrate aspects of arcuate incisions of a cornea that can be formed by the laser surgery system 10, according to many embodiments. FIG. 9A shows an en face view of arcuate incisions within the optical zone of the cornea that can be formed using the laser surgery system 10. The optical zone can be user-adjustable within, for example, the range of 2 mm-11 mm. For asymmetric arcuate incisions, the optical zone can be independently adjustable for each incision. Arc length can be user-adjustable within, for example, the range of 10°-120°.

FIG. 9B shows a cross-sectional view of an arcuate incision in the cornea that can be formed using the laser surgery system 10 and that penetrates the cornea anterior surface and has an uncut posterior portion. FIG. 9C shows a cross-sectional view of an arcuate intrastromal incision in the cornea that can be formed using the laser surgery system 10. The arcuate intrastromal incision has an uncut anterior portion and an uncut posterior portion. Side cut angle can be user-adjustable within, for example, the range of 30°-150°. Uncut posterior and anterior portions can be user-adjustable within, for example, the range of 100 μm-250 μm or 20%-50% of the cornea thickness. Cornea thickness can be measured at the projected intersection of the incision with the cornea anterior/posterior measured at 90° to anterior/posterior cornea surface regardless of what side cut angle is chosen.

Figure 10A:
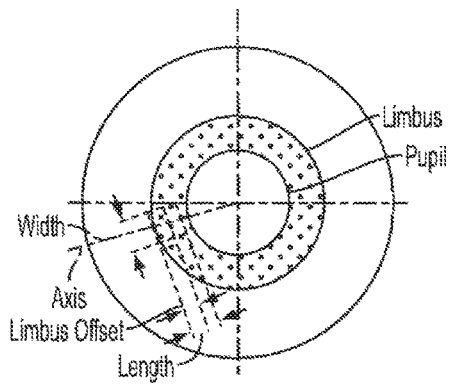
FIGS. 10A, 10B, 10C, 10D, 10E and 10F illustrate aspects of primary cataract surgery access incisions of a cornea that can be formed by the laser surgery system of FIG. 1 according to many embodiments.
Figure 10B:
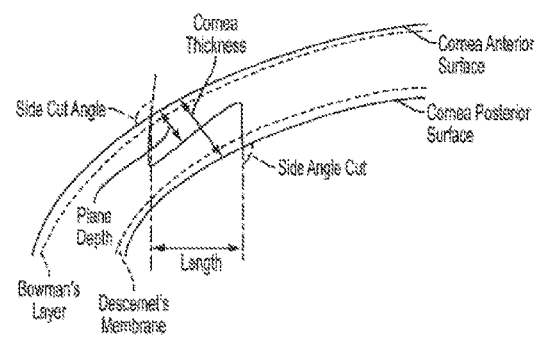
Figure 10C:
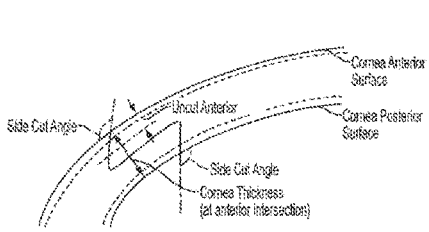
Figure 10D:
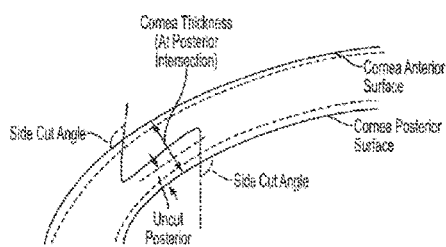
Figure 10E:
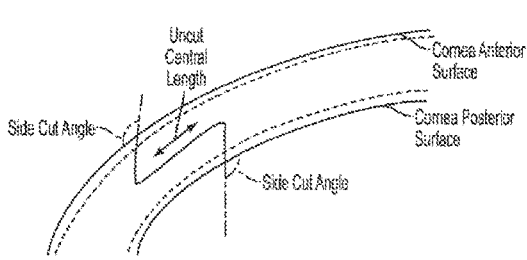
Figure 10F:
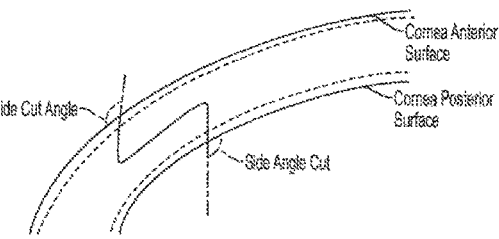

FIG. 10A shows an en face view of a primary cataract incision in the cornea that can be formed using the laser surgery system 10. The primary cataract incision provides access to surgical tools used to, for example, remove a fragmented crystalline lens nucleus and insert in an IOL. FIG. 10B shows a cross-sectional view of a primary cataract incision of the cornea that can be formed using the laser surgery system 10. Limbus offset can be user-adjustable within, for example, the range of 0.0 mm-5.0 mm. Width can be user-adjustable within, for example, the range 0.2 mm-6.5 mm. Length can be user-adjustable within, for example, the range of 0.5 mm 3.0 mm. Side Cut Angle can be user-adjustable within, for example, the range of 30°-150°. Plane depth can be user-adjustable within, for example, the range of 125 μm-375 μm or 25%-75% of the cornea thickness. Length can be defined as the en face view distance between the projected incision intersection with the cornea anterior and the cornea posterior. FIG. 10C shows a cross-sectional view of a primary cataract incision that includes an uncut anterior portion. FIG. 10D shows a cross-sectional view of a primary cataract incision that includes an uncut posterior portion. FIG. 10E shows a cross-sectional view of a primary cataract incision that includes an uncut central length. And FIG. 10F shows a cross-sectional view of a primary cataract incision that includes no uncut portion. Side Cut Angle can be user-adjustable within, for example, the range of 30°-150°. Uncut central length can be user-adjustable within, for example, the range of 25 μm 1000 μm.

Figure 11A:
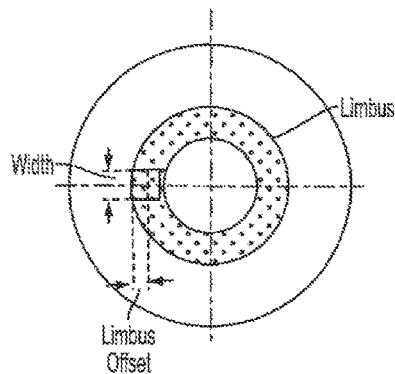
FIGS. 11A, 11B, 11C, 11D and 11E illustrate aspects of sideport cataract surgery access incisions of a cornea that can be formed by the laser surgery system of FIG. 1 according to many embodiments.
Figure 11B:
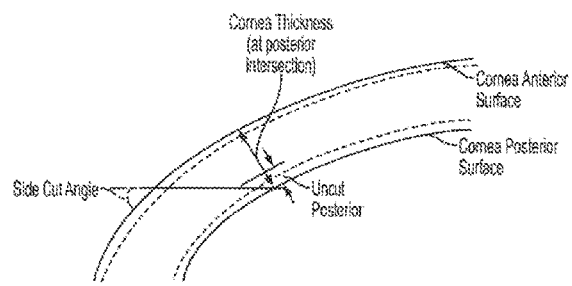
Figures 11C, 11D:
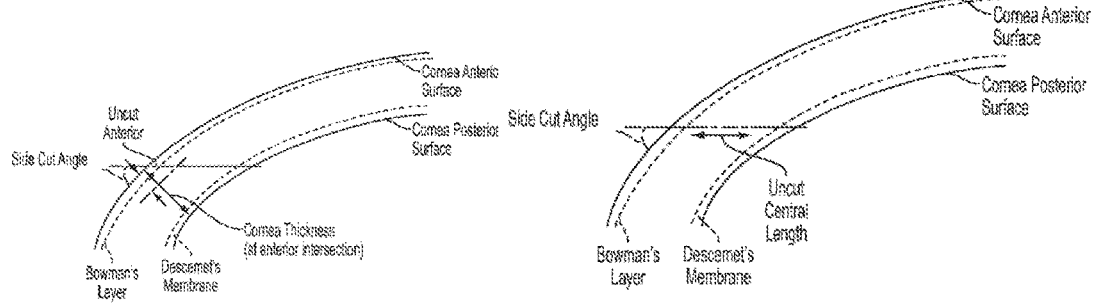
Figure 11E:
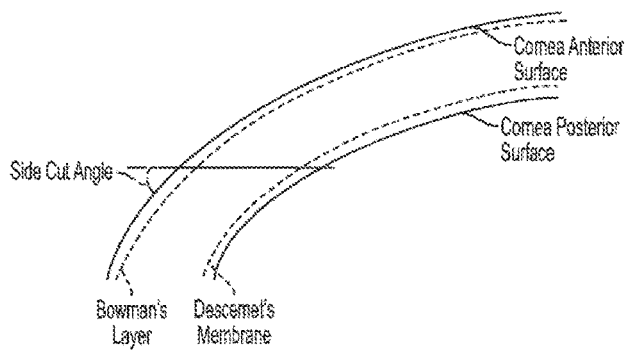

FIG. 11A shows an en face view of a sideport cataract incision in the cornea that can be formed using the laser surgery system 10. The sideport cataract incision provides access for surgical tools used, for example, to assist in the removal of a fragmented crystalline lens. FIG. 11B shows a cross-sectional view of a sideport cataract incision of the cornea that has an uncut posterior portion and can be formed using the laser surgery system 10. Limbus offset can be user-adjustable within, for example, the range of 0.0 mm-5.0 mm. Width can be user-adjustable within, for example, the range 0.2 mm-6.5 mm. Length can be user-adjustable within, for example, the range of 0.5 mm 3.0 mm. FIG. 11C shows a cross-sectional view of a sideport cataract incision that includes an uncut anterior portion. FIG. 11D shows a cross-sectional view of a sideport cataract incision that includes an uncut central length. And FIG. 11E shows a cross-sectional view of a sideport cataract incision that includes no uncut portion. Side Cut Angle can be user-adjustable within, for example, the range of 30°-150°. Uncut central length can be user-adjustable within, for example, the range of 100 μm-250 μm or 20%-50% of the cornea thickness. Cornea thickness can be measured at the projected intersection location of the incision with the cornea anterior/posterior measured at 90° to the anterior/posterior cornea surface regardless of what side cut angle is chosen.

Video and Confocal Imaging of Incision Locations

Although many different imaging techniques may be used in different embodiments, a combination of video/camera imaging and confocal imaging based on pulsed laser raster scanning of the tissue to be treated is preferred.

Figure 13:
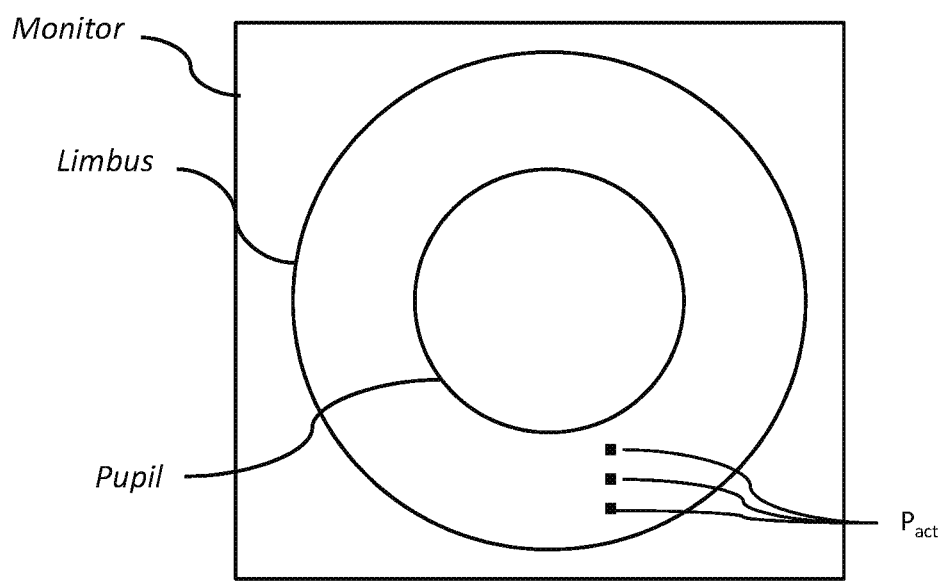
FIG. 13 is a schematic diagram illustrating the en face image of the eye projected onto a monitor using a laser surgery system such as described in FIG. 1.

As illustrated in the embodiment of FIG. 1, video imaging of the tissue to be treated, preferably a human eye, can be achieved by a camera 62 and associated video illumination 64 integrated with the scanning assembly 18. The camera 62 and the beam 28 share a common optical path through the objective lens assembly 20 to the eye. A video dichroic 66 is used to combine/separate the beam 28 with/from the illumination wavelengths used by the camera. In one embodiment, the beam 28 can have a wavelength of between 320 and 370 nm, preferably about 355 nm, and the video illumination 64 can be configured to emit illumination having wavelengths greater than 370 nm, or more than 400 or more than 450 nm. Accordingly, the video dichroic 66 can be configured to reflect the beam between 320 and 370 nm wavelength while transmitting wavelengths greater than 370 nm, thus facilitating video imaging of the eye without interference from beam 28. The resulting video image is preferably an en face image as shown in FIG. 13. The location of the capsulotomy incision and any corneal incision specified by the physician can be projected onto the video image prior to treatment as expected scan locations for each respective incision.

In many embodiments, the imaging of the eye 24 further includes confocally imaging one or more portions of the tissue, preferably the eye, to be treated. Any suitable device, assembly, and/or system, such as described herein, can be used to confocally image one or more portions of the eye or other tissue to be imaged. The confocal imaging methods used herein generally include using a beam source, preferably a pulsed laser source, to generate an electromagnetic radiation beam; propagating the electromagnetic radiation beam to a scanner along an optical path to the eye; focusing the electromagnetic radiation beam to a focal point at a location within the eye; using the scanner to scan, preferably raster scan, the focal point to different locations within the eye; propagating a portion of the electromagnetic radiation beam reflected from the focal point location back along the shared optical path to a sensor; and generating an intensity signal indicative of the intensity of a portion of the electromagnetic radiation beam reflected from the focal point location and propagated to the sensor. The method can include modifying polarization of at least one of the electromagnetic radiation beam and a portion of the electromagnetic radiation beam reflected from the focal point location. The method can include using the polarization-sensitive device to reflect a portion of the electromagnetic radiation beam reflected from the focal point location so as to be incident upon the sensor.

Based on the calibration of the system described herein, the focal point location of the confocally detected light can be related to the physical location of the focal point within the eye, and the location within the eye and the magnitude of the intensity at each location can be used to identify boundaries, edges and layers within the eye. Boundaries, edges and layers may be located in a confocal image by, for instance, Delaunay triangulation and Dijkstra segmentation. These confocal images, including the boundaries, edges and layers can then be displayed to a user as a graphical representation of the areas of the eye to be treated.

In many embodiments, the lens capsule, and optionally a portion or all of the lens, are imaged using confocal imaging, and preferably, these portions include the area of the lens capsule where the capsulotomy will be placed. In general, the parameters necessary to define the capsulotomy are input by a user or physician, and a raster scan with a pulsed laser beam sweeps through the relevant portion of the lens capsule for imaging the lens capsule. Based on the recorded location and magnitude of the confocally reflected intensity measurements at each location, the capsule is identified by image recognition, such as by Delaunay triangulation and Dijkstra segmentation, and the capsule shape is fit to the segmented image. The resulting confocal image of lens may then be shown to the physician for use in visualizing the capsulotomy incision.

Figure 14:
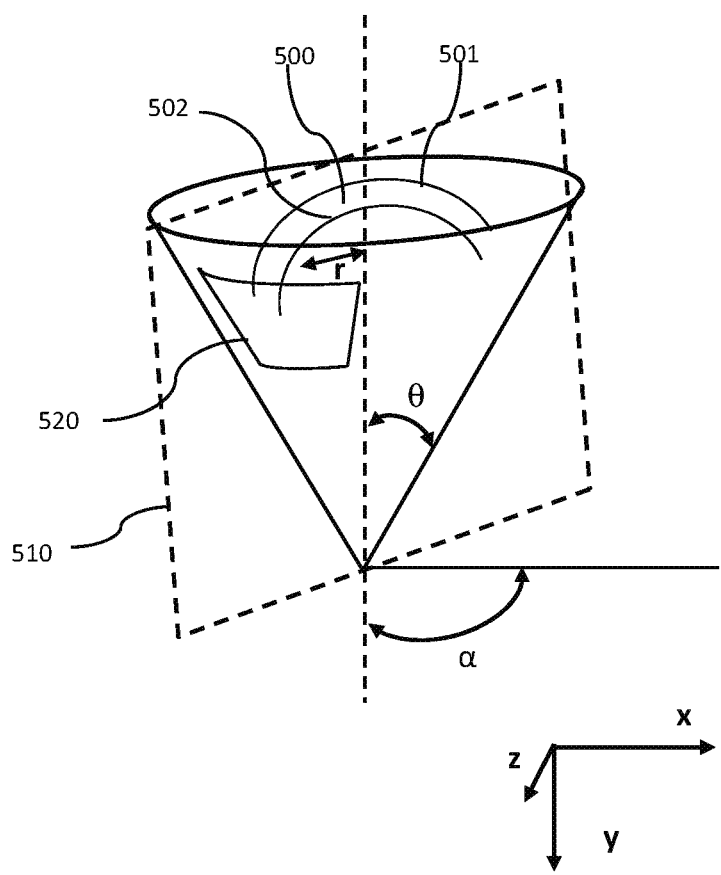
FIG. 14 is a schematic diagram of aspects of a section scan and an along-the-cut scan for imaging areas of a cornea.

In many embodiments, the methods and systems may include confocally imaging a cornea by scanning one or more of portions of the cornea where a primary incision, sideport incision or arcuate incision is to be placed. In a preferred embodiment, one sectional image of the cornea is performed for each selected corneal incision. These images are preferably in the form of a section scan. As shown in FIG. 14, a section scan crosses cornea 500 along plane 510 and measures the confocal intensity at every location of a pulsed laser during the scan. Preferably, a section scan 510 comprises a raster scan of a pulsed laser beam along the cornea 500, including the anterior surface 501 and posterior surface 502, on a vertical plane 510 centered at the cornea incision center and oriented along an incision's meridian. The trajectory goes from deep to shallow, inside the eye, crossing the cornea. The posterior and anterior boundaries of the cornea may be identified in the image by, for instance, Dijkstra segmentation of the image, and the resulting image may be provided to the user.

If the selected corneal incision is an arcuate incision, an "along-the-cut" imaging scan is also preferably performed. An along-the-cut imaging scan may assist a physician in choosing the correct location for the arcuate incision in order to maintain an adequate depth and avoid posterior penetration. The "along the cut" scan preferably has the same conical shape as the arcuate incision and is inclusive of the entire area to be covered arcuate incision. The conical sector in the "along the cut" scan is mapped into a rectangular domain 520 defined by the conical coordinates. The resulting conical image is segmented and fit. Optionally, the resulting fits to the anterior and posterior surfaces of the cornea are used to construct the arcuates, which can then are overlaid on their sections and "along the cut" scans.

In many embodiments, the optical surface of the eye is fit with one or more with one or more of a Fourier transform, polynomials, a spherical harmonics, Taylor polynomials, a wavelet transform, or Zernike polynomials. The optical tissue surface may comprise one or more of the anterior surface of the cornea, the posterior surface of the cornea, the anterior surface of the lens capsule, the posterior surface of the lens capsule, an anterior surface of the lens cortex, a posterior surface of the lens cortex, an anterior surface of the lens nucleus, a posterior surface of the lens nucleus, one or more anterior surfaces of the lens having a substantially constant index of refraction, one or more posterior surfaces of the lens having a substantially constant index of refraction, the retinal surface, the foveal surface, a target tissue surface to correct vision such as a target corneal surface, an anterior surface of an intraocular lens, or a posterior surface of an intraocular lens, for example.

Generating a Treatment Scan

After the relevant portions of the lens, lens capsule and cornea have been imaged, the incisions defined by the physician parameters may be projected onto the image, and a treatment scan of the laser light beam is generated. The treatment scan preferably consists of a continuous set of x, y, z points arranged in space that are designed to carry out the incisions defined by the user. The location of the treatment scans are projected onto at least one of the video and confocal images in order to define the set of expected scan locations of the incisions.

Detecting an Actual Location of a Scan by Luminescence

Certain components of eye tissue absorb light having wavelengths of 370 nm and less and emit red-shifted light (due for instance, to either fluorescence or phosphorescence) at wavelengths greater than 370 nm. The emitted light from the eye tissue is also passed by dichroic 66 in FIG. 12. Thus, when the focal point of beam 28 is scanned across the tissue to be treated, the location of the focal point of beam 28 within the target tissue can be tracked by camera 62 based on the known relationship between the pixels of the camera 62 and the location of the focal point in the treatment space as established by the calibration described above.

Figure 12:
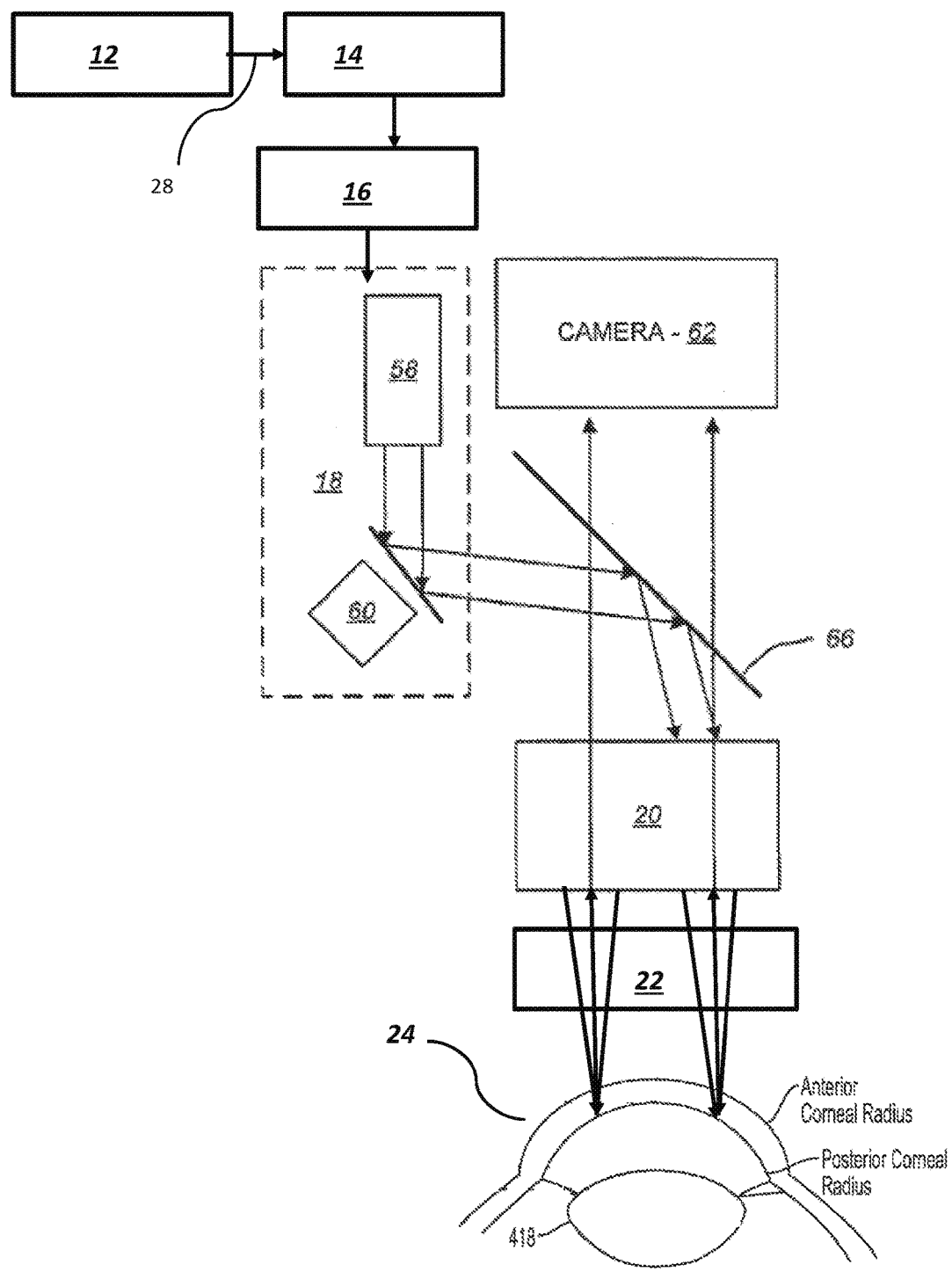
FIG. 12 is a schematic diagram illustrating the use of emission from eye tissue to verify the location scan with a camera of the laser surgery system of FIG. 1.

FIG. 12 schematically illustrates using a luminescence from an eye 24 to obtain a video image of the actual location of a laser scan. Eye 24 includes one or more components that emit light in response to absorbing electromagnetic radiation at wavelengths preferably less than 370 nm. The eye 24 is preferably connected to the objective 20 and scanning assembly 18 via patient interface 22. Light from light source 12 is directed to eye 24 via the confocal assembly 14, the shared optics 16 the scanner 18 and the objective 20. With the focal point of the electromagnetic radiation beam from light source 12 disposed, preferably sequentially, within the eye, the camera 62 is used to detect the actual location of the resulting emission from eye 24 based on the position of the focal point within eye 24. The luminescence is generally detected as one or more pixels, Pact. The observed location of the resulting fluorescent emission can be used in conjunction with calibration data for the camera 62 to determine x and y coordinates of the associated focal point in the treatment space and can be compared to the expected scan location of the incisions.

The camera image of the eye is preferably presented to a user as an en face image, such as shown in FIG. 13 with the pixels, Pact, corresponding to the actual location of the scan illuminated on the image.

The above described methods and systems permit a physician to verify the actual scan location of a contemplated incision in comparison to its expected location and also to confirm that the laser surgical system is adequately calibrated. For example, if the physician desired to make a cut at a predetermined position in an eye, the physical need only enter the necessary parameters to define the location and type of incision the physician intends to make. In one embodiment, the laser surgical system of the present invention is configured to receive these parameters and to project the defined incision onto a video image. In some embodiments, the video image then illustrates the expected position of the incision on the image, by, for instance, illuminating a set of Pixels, PEL, corresponding to the intended location of the incision. The laser system is also preferably configured to carry out a treatment scan configured to make the incision at the predetermined location. As the pulsed laser scans the tissue, a resulting luminescence from the location of the treatment scan is detected and subsequently used to identify the actual location in the eye where the treatment scan was performed. Preferably, the actual location is illustrated on the video image by illuminating a set of pixels, Pact, corresponding to the position of the actual scan. Thus, in some embodiments, if the actual location of the scan differs from the expected location, the physician can visually make this determination by inspection of the video image.

In another embodiment, a warning is issued if a difference between the actual location and the expected location is greater than a predetermined threshold amount. This makes it possible to warn a physician or user, or stop the scan completely, even if the physician is not actively viewing the image.

Preferably, the system and methods are used throughout the entirety of the treatment scan. Specifically, in some embodiments, the progression of the treatment scan is monitored by successive images/frames captured during the treatment. In a preferred embodiment, successive frames of the image capture the progression of the treatment scan in real time. In some embodiments, the difference in detected luminescence between frames track actual location and actual direction of the treatment scan. For example, when a confocal scan is being taken, a video is taken at the same time. In this manner, the system and methods can ensure that the entirety of the incision is placed at its expected location.

The methods described herein also provide a convenient method for confirming that a laser eye surgery system is adequately calibrated. With conventional imaging, a number of safeguards are generally in place to ensure proper calibration; however, a physician may have limited convenient procedures for determining whether the instrument is calibrated. The present invention allows the physician or other user to quickly assess the calibration of the laser surgical system.

It is also noted that the present invention provides a safeguard should the physician inadvertently type in the wrong coordinates for his cuts. In that scenario, the calibration would not necessarily be wrong but the physician would notice that the cutting was not taking place in the correct locations. This event would presumably prompt the physician to double check to see if he typed in the correct geometric coordinates. Further, this method would provide a safeguard should the calibration be off before a procedure by the inadvertent bumping of the camera or things of that nature.

In sum, many embodiments provide a method or system that detects an actual location of a laser scan within an object and verifies whether the laser scan is at the expected location. Other embodiments provide a method or system that detects an actual placement of an ocular incision within an eye and verifies whether the ocular incision is at the intended location. Other embodiments provide a method of verifying the calibration of a laser eye surgical system.

It is to be understood that the present invention is not limited to the embodiment(s) described above and illustrated herein, but encompasses any and all variations explicitly and implicitly derived therefrom. Although not shown in the figures, multiple imaging steps can also be employed in between treatment steps to account for any changes in position and/or size due to treatment and further insure the accurate disposition of laser energy in the target tissue.

All patents and patent applications cited herein are hereby incorporated by reference in their entirety.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

While certain illustrated embodiments of this disclosure have been shown and described in an exemplary form with a certain degree of particularity, those skilled in the art will understand that the embodiments are provided by way of example only, and that various variations can be made without departing from the spirit or scope of the invention. Thus, it is intended that this disclosure cover all modifications, alternative constructions, changes, substitutions, variations, as well as the combinations and arrangements of parts, structures, and steps that come within the spirit and scope of the invention as generally expressed by the following claims and their equivalents.

The invention claimed is:

1. A method of verifying the placement of a laser scan at a predetermined location within an eye, comprising:
    imaging at least a portion of the eye, the resulting image comprising the predetermined location;
    identifying the predetermined location in the image, thereby establishing an expected scan location of the laser scan in the image;
    performing the laser scan on the eye by scanning a focal point of a laser beam in a scanned area, the laser beam having a wavelength;
    detecting a luminescence from eye tissue in the scanned area of the eye without receiving or detecting a reflected light from the eye tissue having a same wavelength as the wavelength of the laser beam, and identifying an actual scanned location within the image of the portion of the eye based on the detected luminescence; and
    verifying whether the laser scan was at the predetermined location based on a difference between the actual scanned location in the image of the portion of the eye and expected scan location in the image of the portion of the eye.

2. The method of claim 1, wherein the laser beam is a pulsed laser beam having a wavelength of 320 nm to 370 nm.

3. The method of claim 1, wherein the luminescence has a wavelength of 400 nm or more.

4. The method of claim 1, wherein the image comprises an array of pixels.

5. The method of claim 4, wherein the expected location comprises one or more pixels selected from amongst the array of pixels.

6. The method of claim 4, wherein the actual scanned location comprises one or more pixels selected from the array of pixels.

7. The method of claim 4, wherein the method further comprises:
    periodically re-imaging the object, thereby obtaining one or more successive images of the object; and
    identifying the actual scanned location by comparing a detected luminescence of a same pixel in the array between two or more of the successive images.

8. The method of claim 7, wherein the method further comprises:
    identifying a direction of the scan by comparing an actual scanned location in between two or more of the successive images.

9. The method of claim 1, where verifying the laser scan at the predetermined location comprises determining whether a distance between the actual scanned location and the expected scan location is greater than a predetermined threshold.

10. A method of verifying the placement an ocular incision by a laser surgical system at a predetermined location within an eye, the method comprising:
    imaging at least a portion of the eye, the resulting image comprising the predetermined location for a laser scan corresponding to the ocular incision;
    identifying the predetermined location in the image, thereby establishing an expected scan location of the laser scan in the image;
    performing the laser scan on the eye by scanning a focal point of a laser beam in a scanned area of the eye, the laser beam having a wavelength, the laser scan being configured in a scan pattern for performing the ocular incision;
    detecting a luminescence from eye tissue in the scanned area of the eye without receiving or detecting a reflected light from the eye tissue having a same wavelength as the wavelength of the laser beam, and identifying an actual scanned location within the image of the portion of the eye based on the detected luminescence; and
    verifying the placement of an ocular incision based on the difference between the actual scanned location in the image of the portion of the eye and expected scan location in the image of the portion of the eye.

11. The method of claim 10, wherein the laser beam is a pulsed laser beam having a wavelength of 320 nm to 370 nm.

12. The method of claim 10, wherein the luminescence has a wavelength of 400 nm or more.

13. The method of claim 10, wherein the image comprises an array of pixels.

14. The method of claim 13, wherein the expected scan location comprises one or more pixels selected from amongst the array of pixels.

15. The method of claim 13, wherein the actual location comprises one or more pixels selected from the array of pixels.

16. The method of claim 13, wherein the method further comprises:
   periodically re-imaging the eye, thereby obtaining one or more successive images of the eye; and
   identifying the actual scanned location by comparing a detected luminescence of a same pixel in the array between two or more of the successive images.

17. The method of claim 16, wherein the method further comprises:
   identifying a direction of the scan by comparing an actual scanned location in between two or more of the successive images.

18. The method of claim 10, where verifying the laser scan at the predetermined location comprises determining whether a distance between the actual scanned location and the expected scan location is greater than a predetermined threshold.

19. A laser eye surgical system, comprising:
   a laser source for generating a pulsed laser beam having a wavelength;
   an imaging system comprising a detector;
   shared optics configured for directing the pulsed laser beam to an eye, including a dichroic reflector configured to reflect light having a same wavelength as the wavelength of the laser beam and to pass light within a wavelength range longer than the wavelength of the laser beam, the dichroic reflector being disposed between the eye and the detector;
   a controller operatively coupled to the laser source, the imaging system and the shared optics, wherein the controller is configured to control the laser eye surgical system to:
   (a) receive one or more parameters defining one or more ocular incisions;
   (b) image at least a portion of the eye with the imaging system and identify an expected scan location within the image corresponding to the one or more ocular incisions based on the one or more parameters;
   (c) scan a focal point of the pulsed laser beam in a region of the eye using the shared optics;
   (d) detect a luminescence from eye tissue in the scanned region of the eye using the imaging system, without receiving or detecting a reflected light from the eye tissue having a same wavelength as the wavelength of the laser beam;
   (e) identify the actual scanned location within the image based on the detected luminescence of the eye tissue;
   (f) determine a difference between the actual scanned location in the image of the portion of the eye and the expected scan location in the image of the portion of the eye; and
   (g) provide a warning to a user of the laser eye surgical system when the difference is greater than a predetermined threshold value.

20. The laser eye surgical system of claim 19, wherein the laser beam has a wavelength of 320 nm to 370 nm.

21. The laser eye surgical system of claim 19, wherein the luminescence has a wavelength of 400 nm or more.

22. The laser eye surgical system of claim 19, wherein the image comprises an array of pixels.

23. The laser eye surgical system of claim 22, wherein the expected scan location comprises one or more pixels selected from amongst the array of pixels.

24. The laser eye surgical system of claim 22, wherein the actual scanned location comprises one or more pixels selected from the array of pixels.

25. The laser eye surgical system of claim 19, further comprising a display, wherein the laser eye surgical system is configured to display the image of the eye to a user of the laser eye surgical system and to identify in the image the expected scan location and the actual scanned location.

26. The laser eye surgical system of claim 22, wherein the controller is further configured to:
   periodically re-image the eye, thereby obtaining one or more successive images; and
   identify the actual scanned location by comparing a detected luminescence of a same pixel in the array between two or more of the successive images.

27. The laser eye surgical system of claim 26, wherein the controller is further configured to:
   identify direction of the scan by comparing an actual scanned location in between two or more of the successive images.

28. The laser eye surgical system of claim 19, wherein the controller is configured to verify the laser scan is at the predetermined location when a distance between the actual scanned location and the expected scan location is within a predetermined threshold.

29. The laser eye surgical system of claim 19, further comprising a patient interface, wherein the pulsed laser beam is provided to the eye from the shared optics via the patient interface, and wherein luminescent light from the eye tissue produced in response to the pulsed laser beam is provided to the detector via the patient interface.

30. The laser eye surgical system of claim 19, further comprising a dichroic element configured to direct the pulsed laser light beam at a first frequency to the eye and to direct luminescent light from the eye tissue produced in response to the pulsed laser beam to the detector.

31. The method of claim 1, further comprising displaying the image, and identifying in the image the expected scan location and the actual scanned location.

32. The method of claim 1, further comprising:
   providing the laser beam to the eye via a patient interface; and
   providing luminescent light from the eye tissue produced in response to the laser beam to a camera via the patient interface.

33. The method of claim 1, further comprising:
   directing the pulsed laser light beam at a first frequency to the eye via a dichroic element; and
   directing luminescent light from the eye tissue produced in response to the laser beam to a camera via the dichroic element.

34. The method of claim 10, further comprising displaying the image, and identifying in the image the expected scan location and the actual scanned location.

35. The method of claim 10, further comprising:
   providing the laser beam to the eye via a patient interface; and
   providing luminescent light from the eye tissue produced in response to the laser beam to a camera via the patient interface.

36. The method of claim 10, further comprising:
   directing the pulsed laser light beam at a first frequency to the eye via a dichroic element; and directing luminescent light from the eye tissue produced in response to the laser beam to a camera via the dichroic element.

\* \* \* \* \*